US011413465B2

(12) United States Patent
Kiani

(10) Patent No.: US 11,413,465 B2
(45) Date of Patent: Aug. 16, 2022

(54) FREE-FLOATING MILLIMETER-SIZED DISTRIBUTED IMPLANTABLE GASTRIC SEEDS

(71) Applicant: The Penn State Research Foundation, University Park, PA (US)

(72) Inventor: Mehdi Kiani, State College, PA (US)

(73) Assignee: The Penn State Research Foundation, University Park, PA (US)

(*) Notice: Subject to any disclaimer, the term of this patent is extended or adjusted under 35 U.S.C. 154(b) by 2 days.

(21) Appl. No.: 17/047,150

(22) PCT Filed: Apr. 11, 2019

(86) PCT No.: PCT/US2019/026887
§ 371 (c)(1),
(2) Date: Oct. 13, 2020

(87) PCT Pub. No.: WO2019/200031
PCT Pub. Date: Oct. 17, 2019

(65) Prior Publication Data
US 2021/0162223 A1     Jun. 3, 2021

Related U.S. Application Data

(60) Provisional application No. 62/657,113, filed on Apr. 13, 2018.

(51) Int. Cl.
*A61N 1/372* (2006.01)
*G16H 40/67* (2018.01)
(Continued)

(52) U.S. Cl.
CPC ....... *A61N 1/37217* (2013.01); *A61N 1/0509* (2013.01); *A61N 1/36007* (2013.01);
(Continued)

(58) Field of Classification Search
CPC .......................... A61N 1/37217; G16H 40/67
(Continued)

(56) References Cited

U.S. PATENT DOCUMENTS 9,682,233 B2   6/2017   Knudson et al.
2004/0193229 A1   9/2004   Starkebaum et al.
(Continued)

FOREIGN PATENT DOCUMENTS

CN     100403972 C    7/2008

OTHER PUBLICATIONS

International Search Report dated Jul. 3, 2019; International Application No. PCT/US2019/026887.
(Continued)

*Primary Examiner* — Nadia A Mahmood
(74) *Attorney, Agent, or Firm* — Dinsmore & Shohl LLP

(57) ABSTRACT

A method and system for gastric stimulation and imaging for a user. The system having an array of millimeter-sized gastric seeds implanted in a stomach area of a user. Each gastric seed is ultrasonically powered and communicates using a transducer, and the transducer has a recorder to measure a bioelectrical activity in the stomach area of the user. A wearable unit (WU) is worn or carried by the user, and the WU wirelessly powers the gastric seeds. The WU wirelessly communicates with the gastric seeds, and the gastric seeds communicate a parameter to the WU based on the bioelectrical activity. Received pulses by the seeds can be used to localize the position of the seeds and guide the wireless power/data transmission in a self-image-guided manner. A processing unit (PU) wirelessly communicates with the WU, and the WU communicates the parameters from the gastric seeds to the PU.

26 Claims, 17 Drawing Sheets

(51) Int. Cl.
*G16H 30/40* (2018.01)
*A61N 1/05* (2006.01)
*A61N 1/36* (2006.01)
*A61N 1/378* (2006.01)
*H04B 11/00* (2006.01)

(52) U.S. Cl.
CPC ....... *A61N 1/3787* (2013.01); *A61N 1/37205* (2013.01); *G16H 30/40* (2018.01); *G16H 40/67* (2018.01); *H04B 11/00* (2013.01)

(58) Field of Classification Search
USPC .......................................................... 607/40
See application file for complete search history.

(56) References Cited

U.S. PATENT DOCUMENTS

| | | |
|---|---|---|
| 2008/0234599 A1 | 9/2008 | Chiao et al. |
| 2012/0041310 A1 | 2/2012 | Towe |
| 2012/0203306 A1* | 8/2012 | Sarvazyan ......... A61N 1/36062 607/61 |
| 2013/0226259 A1 | 8/2013 | Penner |
| 2014/0277249 A1 | 9/2014 | Connor |

OTHER PUBLICATIONS

Aydin Farajidavar; A miniature bidirectional telemetry system for in-vivo gastric slow wave recordings; Published in final edited form as: Physiol Meas. Jun. 2012 ; 33(6): N29-N37. doi:10.1088/0967-3334/33/6/N29.

Gastric Electrical Stimulation; Sutter Health CPMC; 4 pages.

J.Hajer and M. Novak; Development of an Autonomous Endoscopically Implantable Submucosal Microdevice Capable of Neurostimulation in the Gastrointestinal Tract; Gastroenterology Research and Practice vol. 2017, Article ID 8098067, 8 pages https://doi.org/10.1155/2017/8098067.

Soffer; Gastric Wlectrical Stimulation for Gastroparesis; Neurogastroenterol Motil, vol. 18 No. 2 Apr. 2012 pISSN: 2093-0879 eISSN: 2093-0887 http://dx.doi.org/10.5056/jnm.2012.18.2.131.

Niranchan Paskaranandavadivel1, Rui Wang2, Shameer Sathar1, Gregory O'Grady1, Leo K Cheng1,3, and Aydin Farajidavar; Multi-channel wireless mapping of gastrointestinal serosal slow wave propagation; Published in final edited form as: Neurogastroenterol Motil. Apr. 2015; 27(4): 580-585. doi:10.1111/nmo.12515.

Sanchali Debm PhD; Shou-Jiang Tang, MD2, Thomas L. Abell, MD2, Smitha Rao, PhD1, Wen-Ding Huang, PhD1, S.D. Filip To, PhD4, Christopher Lahr, MD3, and Jung-Chih. Chiao, PhD1 1Department; An endoscopic wireless gastrostimulator; Published in final edited form as: Gastrointest Endosc. Feb. 2012 ; 75(2): 411-415. e1.doi:10.1016/j.gie.2011.09.052.

Deb Sanchali, PhD1, Shou-jiang Tang, MD2, Thomas L. Abell, MD2, Tyler McLawhorn4, Wen-Ding Huang, PhD1, Christopher Lahr, MD3, S.D. Filip To, PhD5, Julie Easter4, and J.-C. Chiao, PhD1 Jackson, Mississippi; Development of innovative techniques for the endoscopic implantation and securing of a novel, wireless, miniature gastrostimulator (with videos); Published in final edited form as: Gastrointest Endosc. Jul. 2012 ; 76(1): 179-184. doi:10.1016/j.gie.2012.03.177.

\* cited by examiner

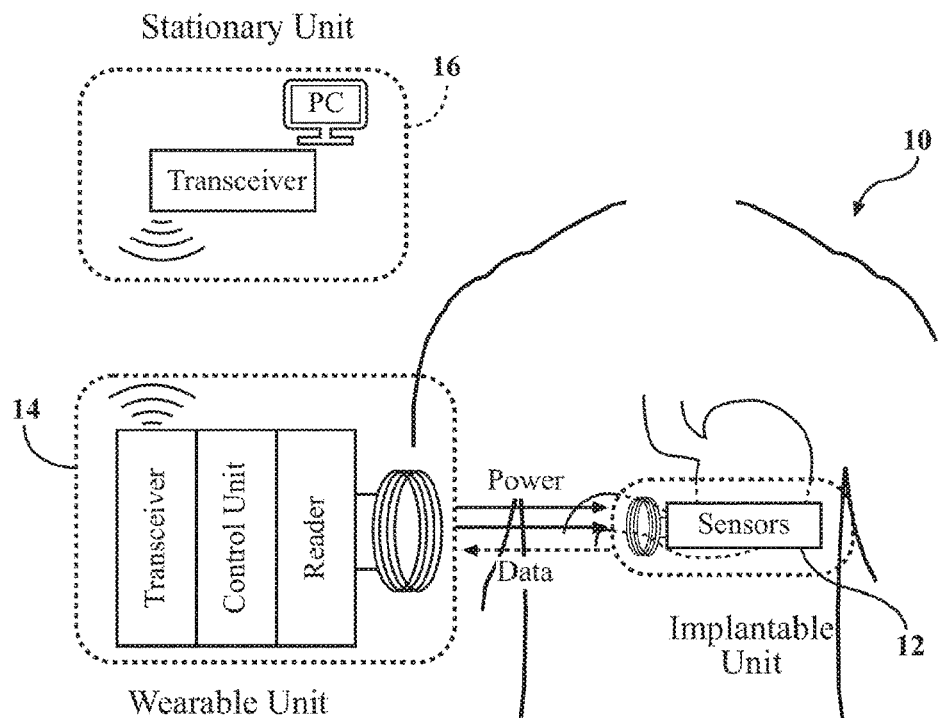
FIG. 1
PRIOR ART
FIG. 2
PRIOR ART
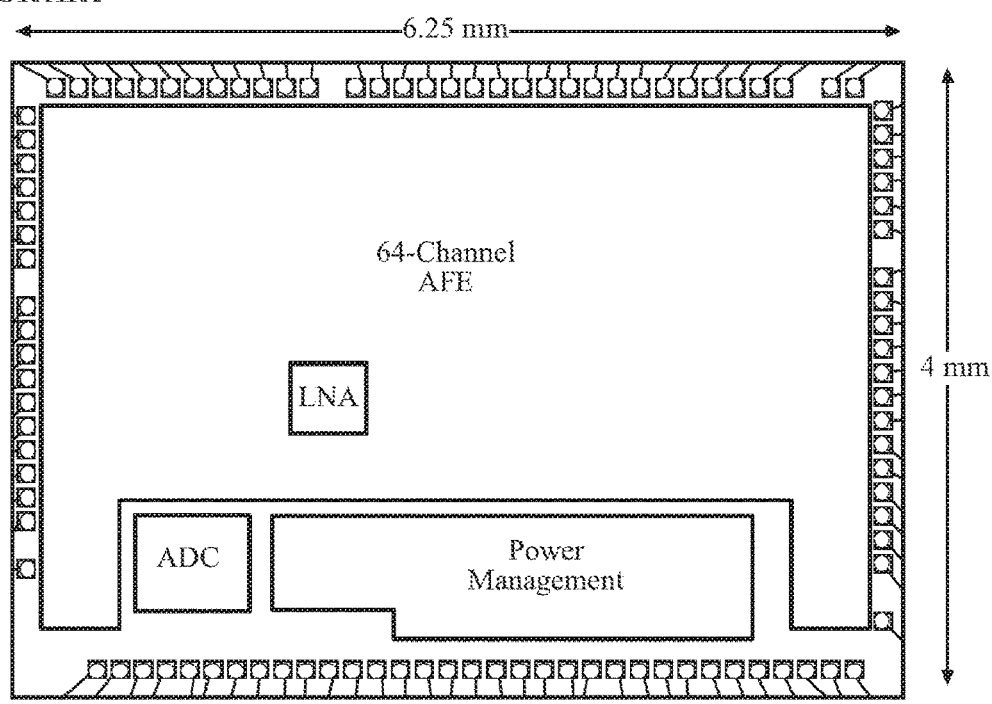

FIG. 7
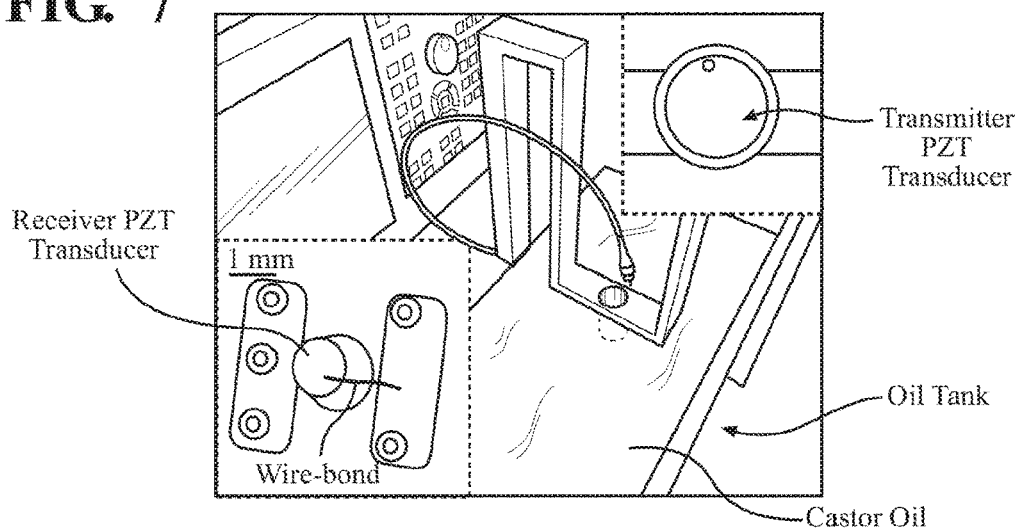
FIG. 8
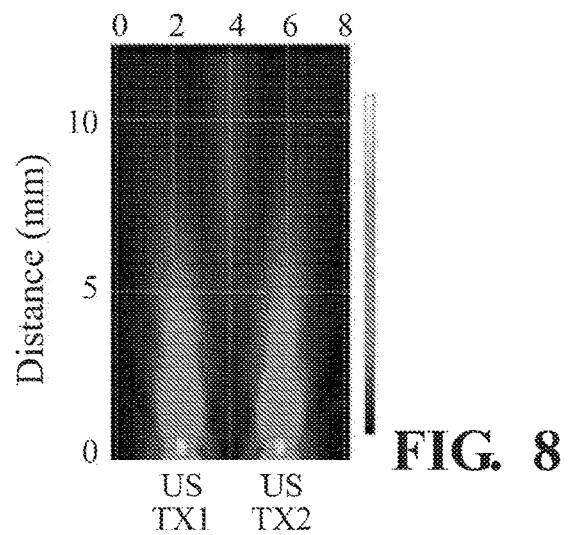
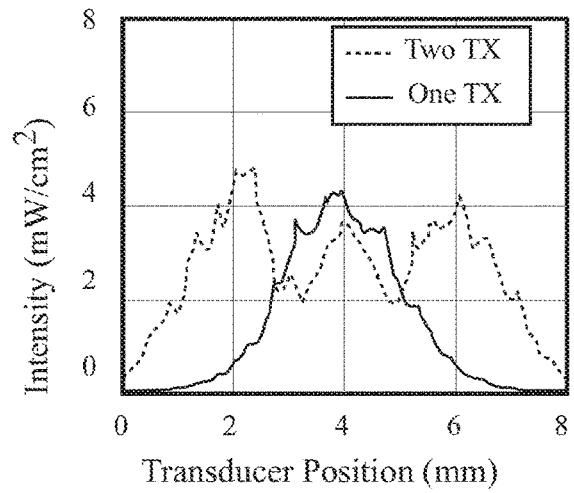
FIG. 9

FIG. 10
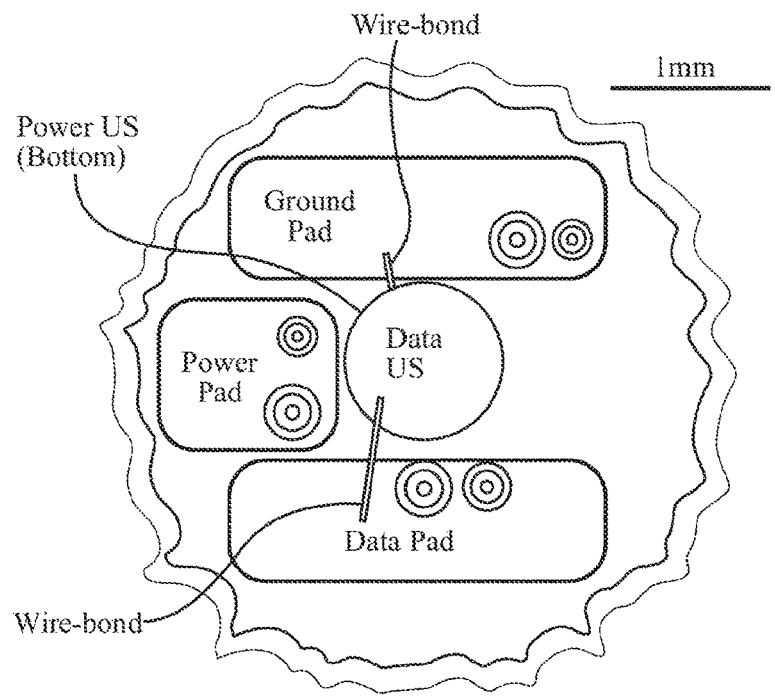
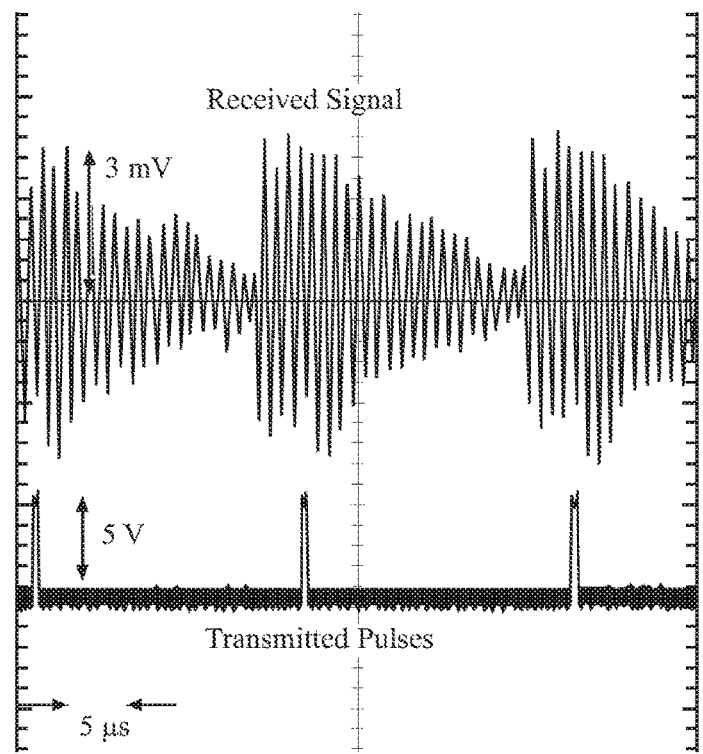
FIG. 11

FIG. 14
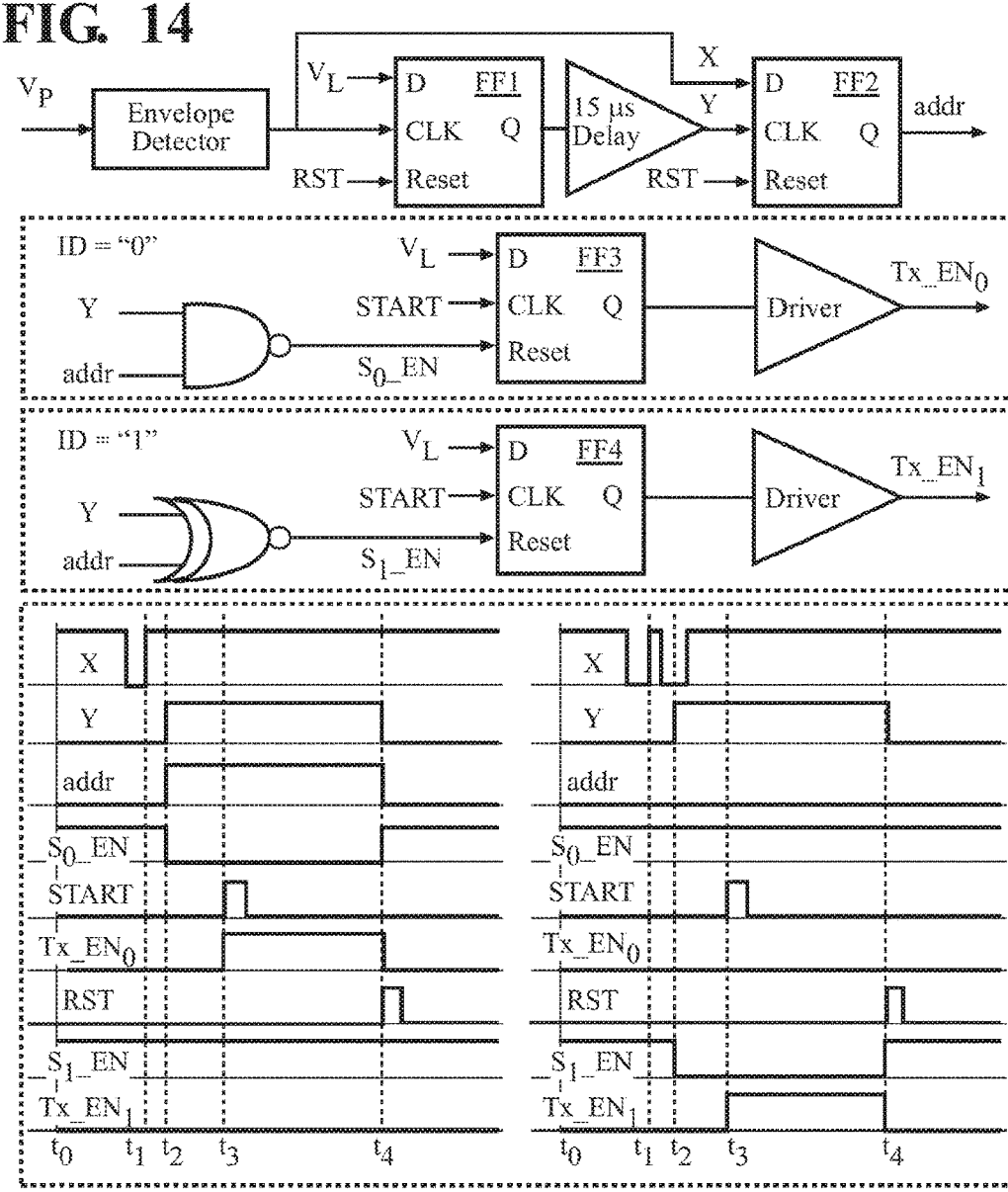
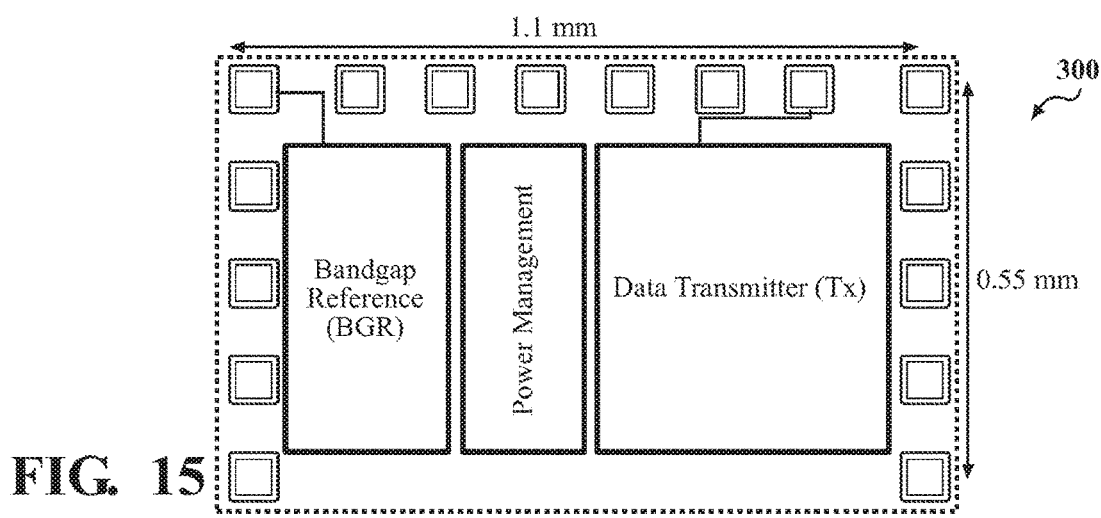
FIG. 15

FREE-FLOATING MILLIMETER-SIZED DISTRIBUTED IMPLANTABLE GASTRIC SEEDS

REFERENCE TO RELATED APPLICATION

This application is the U.S. National Stage of PCT/US2019/026887 filed Apr. 11, 2019, which claims priority to U.S. Provisional Patent Application Ser. No. 62/657,113, filed Apr. 13, 2018, the entire content of both are incorporated herein by reference in their entirety.

FIELD OF THE INVENTION

The present invention generally relates to the field of implantable technology for recording and stimulation of gastric slow waves (SWs) as well as ultrasound interrogation (wireless power/data) of miniaturized implantable devices.

BACKGROUND OF THE INVENTION

Gastric contractions are initiated and coordinated by an underlying bioelectrical activity, termed slow waves (SWs). Aberrant SW patterns (dysrhythmias) have been associated with gastric dysmotility in several significant gastric motility disorders, notably gastroparesis (GP), chronic nausea and unexplained vomiting, and functional dyspepsia (FD). The GP is a chronic debilitating disease, with symptoms including continuous nausea and vomiting, affecting more than 1.5 million people in the United States (US). Up to 30-50% and 16-30% of patients with Type 1 and Type 2 diabetes suffer from the GP or related symptoms, respectively. This number is increasing due to the diabetes epidemic, with hospitalizations rising 150% in the last decade with major increase in the associated costs. The FD is a chronic disorder characterized by upper abdominal pain, bloating and early satiety. The FD is highly prevalent, affecting up to 15-30% of the US population, with vast associated economic burden. The FD is also associated with gastric emptying impairments in up to 20-40% of FD patients, and among several putative mechanisms, dysrhythmic SW activity has been implicated in some 33-83% of FD patients. The diagnoses of FD and GP are challenging, often requires multiple clinical visits and investigations including radioisotope scans, endoscopy, contrast studies, ultrasound, and SmartPill. However, these diagnostic strategies represent a process of exclusion, rather than analyzing fundamental mechanisms, and none allows real-time continuous monitoring of the SW dysrhythmias in the conscious users that may be directly contributing to pathophysiology and symptoms.

High-resolution mapping technologies have become a fundamental tool for accurately defining electrophysiological properties in multiple fields, including electromyography and electrocardiography. These high-resolution mapping technologies have also recently been advocated as a tool to reveal the mechanisms underlying gastric dysrhythmias, which have been poorly understood using past techniques. Prominent studies have recently revealed a surprising complexity underlying gastric dysrhythmias, comparable to cardiac dysrhythmias, and including complex focal activities and re-entrant patterns. Translating these advances to the clinic to clarify the role of dysrhythmias in conditions such as GP, and FD is now a research priority in this field. Translational advances in high-resolution mapping are also anticipated to guide progress in the therapy field and are critically needed because current therapies for the GP and FD have poor efficacy.

Despite 100 years of intensive investigations, the clinical significance of gastric dysrhythmia remains poorly understood. Current gastrointestinal (GI) therapies, including gastric electrical stimulation (GES) and various pharmaceuticals are delivered and adjusted through trial and error in an open-loop fashion. Consequently, various researchers have reported conflicting therapeutic effects and the role of some of these therapies remains controversial. To better elucidate the pathophysiological significance of gastric electrical abnormalities, chronic studies in the conscious users, in fasting and fed states, are necessary. Non-invasive/indirect techniques such as cutaneous recordings, also called electrogastrography (EGG) and high-resolution EGG (HR-EGG), have limited accuracy and are highly prone to motion artifacts. The SWs taken directly from the stomach currently provide the only reliable and spatially descriptive data. These techniques are invasive in comparison to the EGG and HR-EGG. High-resolution mapping of the SWs has been a critical recent advance, allowing a new era in accurate analysis of the dysrhythmic onset and maintenance. However, the current high-resolution direct mapping approaches are highly invasive, and therefore, cannot be applied in chronic animal studies or patients. Existing serosal or mucosal recording systems currently transmit signals through wires traversing either through the abdominal wall or through a natural orifice. These wires can act as a conduit for infection, induce discomfort, become displaced, and restrict mobility due to their connection to bulky acquisition systems; hence, the monitoring period is often limited to the anaesthetized state of the animal or patient.

The Pennsylvania State University in collaboration with the New York Institute of Technology (NYIT) have developed wireless and implantable technologies to acquire SWs from the GI tract. This technology is composed of 1) a wireless 64-channel implant (size: $30 \times 10 \times 6.7 \approx 2000 \text{ mm}^3$) that is placed in the stomach submucosa space through an endoscopic procedure, 2) a wearable unit that powers the implant by inductive coupling and receives the SWs via inductive backscattering, and 3) a stationery unit that is connected to a computer and can display the SWs in real time (FIG. 1). An implantable Complementary Metal-Oxide-Semiconductor (CMOS) Application-Specific Integrated Circuit (ASIC) (i.e. CMOS-ASIC) integrates 64 low-noise amplifiers (LNAs) and filters, an 8-bit analog-to-digital-converter (ADC), a power management circuit, and a data transmitter (FIG. 2). The CMOS-ASIC connects to an array of flexible electrodes to wirelessly record and then map the SWs. Although this system acquires the gastric SW activity, it still suffers from the following multiple shortcomings, such as 1) due to the stomach motility and the implant's bulkiness, the electrodes (or implant) detach from the muscle's surface (or submucosa space), resulting in signal loss or a serious complication, 2) due to the implant's size and implantation procedure, enteric nervous system under the submucosa space can be damaged, resulting into failure of the implantation procedure or signal acquisition, 3) due to limitations in the endoscopic implantation method (i.e. making a pocket in the submucosa space) this system can acquire the SWs from a limited portion of the GI tract (i.e., limited spatial coverage), and 4) this system can only record gastric SWs without any stimulation capability, i.e. it is a open-loop system. In addition, gastric motility cannot be measured by this system. The above-discussed existing approaches do not use a distributed addressable network, and employ either power-hungry carrier-based data transfer or weak backscattering via load modulation, which serves short distances.

The current high-resolution mapping approaches are highly invasive in that electrode wires traversing the abdominal wall or a natural orifice pose risks of discomfort, dislodgement or infection. Thus, it is desirable to enhance the current therapies to provide a better solution in order to overcome limitations of the existing technologies.

SUMMARY OF THE INVENTION

As a result, closed-loop methods are required to enhance the existing therapies. For instance, synchronized closed-loop GES has been applied on anesthetized canine models to modulate gastric contractions and enhance gastric motility. Robust and real-time acquisition of SW data in the conscious patients can be used as the feedback signal to develop a closed-loop therapy. This disclosure outlines a free-floating, minimally invasive, implantable technology for both recording and stimulation of the gastric SWs at a large scale inside the whole stomach using a network of ultrasonically or inductively powered and communicated millimeter-sized implants called gastric seeds. This technology features ultrasonic self-regulated integrated power management, low-power pulse-based data transfer, addressability of each gastric seed in the network, and a self-image-guided ultrasound interrogation technique for robust and efficient wireless power and data transfer to any network of miniaturized implants particularly in actively mobile environments like stomach.

The proposed gastric seeds are 1) small (millimeter scale), light, free-floating, and wireless to minimize the motion artifacts, tissue damage, and risk of infection and expulsion, 2) modular to acquire SWs from the whole stomach through independent interrogation of each addressable gastric seed with unique identification (IDs), 3) capacitively or electrically coupled to the tissue, and 4) implanted in the stomach submucosa space through an endoscopic procedure. The gastric seeds either use ultrasound or RF signals (inductive link) for wireless power and bidirectional data transmission for a distributed addressable network as discussed in this disclosure. This disclosure discusses ultrasonic wireless power/data transmission, but similar techniques can also be employed for inductive power/data transmission. When the gastric seeds communicate with ultrasound using sharp pulses, the received pulses are used to image the location of the gastric seeds and to measure gastric motility of the user as well.

The proposed technology is briefly discussed herewith and has three key modules (i.e. a network of implantable gastric seeds, a Wearable Unit (WU), and a Processing Unit (PU)). An array of millimeter-scale gastric seeds is placed in the stomach's submucosa layer of a user. In accordance with the present disclosure, the volume of an individual gastric seed may be 10 mm$^3$ or less in scale, and not in cm$^3$ scale or more. As discussed above, the wireless 64-channel implant has an approximate volume of about 2000 mm$^3$ and is not be considered as millimeter-sized according to this disclosure. The millimeter-sized gastric seeds according to this disclosure may be defined as having a volume range from about 1 mm$^3$ to 10 mm$^3$. None of the millimeter-sized gastric seeds of this disclosure have a volume of more than 100 mm$^3$. The gastric seeds are placed either surgically e.g. endoscopically (minimally invasive) or through other suitable techniques in the submucosa layer or other layers of the stomach of the user. In some embodiments, the gastric seeds may be placed in a plurality of layers of the user's stomach. The gastric seeds may be positioned in a defined area of the stomach, equally distributed throughout the stomach, or have a varying concentration in one layer/area of the stomach in comparison to other layers/areas of the stomach. In a non-limiting example, the gastric seeds may be partially, subtotally, or completely implanted or embedded in one or more layers of the stomach.

In comparison to the above-discussed existing technologies, the small size of the gastric seeds does not interfere with stretching and contractions of the gastrointestinal (GI) tract muscles in the stomach. These muscle movements partly occur due to peristalsis and segmentation (mixing). The small size also reduces the likelihood of any damage caused by the gastric seeds to the user's stomach due to muscle movement or the user's normal routine lifestyle.

The gastric seeds are operable to measure the gastric SWs, wirelessly transmit the measured value, and to stimulate the stomach tissues based on wirelessly received data to influence gastric motility related disorders. A human user's stomach consists of different layers. These layers, starting from the innermost layer, are named mucosa, sub-mucosa, muscularis externa, and the serosa. The gastric seeds placed in one stomach layer may be able to measure the gastric SWs and/or stimulate the stomach tissues of another stomach layer. Moreover, the gastric seeds may be powered wirelessly to meet the operational power requirements of the gastric seeds. Bidirectional wireless communication satisfies all the data and power requirements of the gastric seeds. Thus, each of the in-vivo gastric seeds is a discreet unit that does not require any wired circuitry for power/data communication extraneous to the stomach layers.

The second module of the proposed technology is the external WU. The external WU is a flexible printed circuit board (PCB) in the form of a bellyband worn by the user. In some embodiments, the WU may be not be flexible and/or have a self-contained cuboidal, spherical, or cylindrical or other suitable form/shape. In other embodiments, the user may carry the WU instead of wearing the WU. The shape and flexibility of the WU should be determined such that the WU is able to wirelessly communicate with and power each implanted gastric seed. Each gastric seed within the stomach has a unique address and location that is used by the WU for identification. The WU receives the measured value of the gastric SWs from each gastric seed and transmits the desired stomach tissue stimulation parameters. The WU also delivers a minimum power to each gastric seed regardless of its location (whole stomach) and alignment/orientation. In some embodiments, each gastric seed is aligned/oriented with respect to the WU. In a non-limiting example, the gastric seed(s) and the WU are parallel or perpendicular to each other for maximum wireless power/data transmission efficiency. Although not all the implanted gastric seeds may be totally parallel or perpendicular with respect to the WU, the WU is operable to deliver a predetermined minimum power and bidirectional data transmission for each gastric seed.

The third module of the proposed technology is the PU that is located a few meters from the user to wirelessly receive the measured SWs from the WU for real-time display and mapping the stomach activity. The PU has the location/coordinate parameter information, address of each gastric seed and uses it to generate a stomach activity map of the user. The PU acts as a central processing unit of the proposed technology. The PU receives and records the measured SWs, and determines the amount and duration of tissue stimulation that each of the gastric seed may deliver to improve upon gastric motility disorders of the user. The PU transmits the stimulation and power related parameters for each gastric seed to the WU that further transmits this information to each gastric seed. Thus, it is a closed-loop system that measures the SWs in real time, generates the stomach activity map, and based on the map determines and stimulates the stomach tissues of the user.

BRIEF DESCRIPTION OF THE DRAWINGS

FIG. 1 shows a prior art wireless system for slow wave (SW) recording;

FIG. 2 shows an embodiment of an implantable sensor unit of FIG. 1;

FIG. 7 is a drawing of an experimental set-up of the present disclosure;

FIG. 8 shows two ultrasonic (US) transmitters operating in far-field region;

FIG. 9 is a graph showing ultrasonic (US) intensity of transmitters;

FIG. 10 is a top view of a gastric seed according to an embodiment of this disclosure;

FIG. 11 is a graph of a wireless pulse-based data transmission;

FIG. 14 is a schematic of a data transmitter and a graph showing operational waveforms of the data transmitter;

FIG. 15 is a view of an embodiment of a gastric seed chip with only power and data transfer capabilities according to this disclosure;

DETAILED DESCRIPTION OF THE INVENTION

Figure 3:
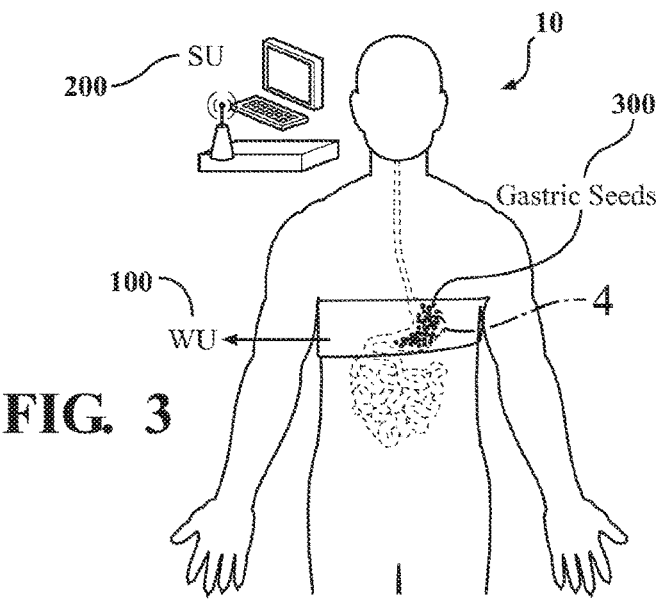
FIG. 3 shows a user with an embodiment according to this disclosure.
Figure 4:
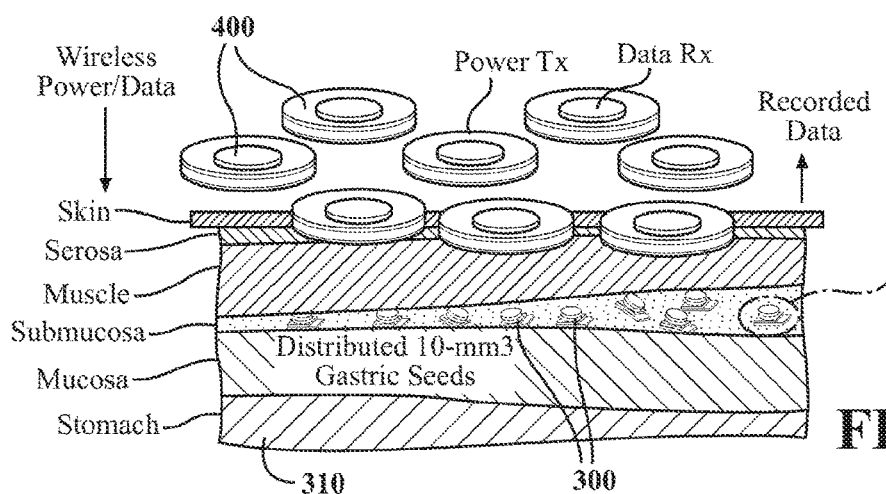
FIG. 4 is an enlarged view of an inset in FIG. 3.

The proposed technology is discussed herewith in detail in reference to the Figures. As discussed above, the proposed new paradigm has a large-scale gastric interfacing to eliminate the aforementioned shortcomings of the prior art by developing a network of distributed, minimally invasive, ultrasonically and/or inductively powered/communicated implants (called gastric seeds). The key modules of the proposed technology shown in FIG. 3 include a network of the implantable gastric seeds 300, a Wearable Unit (WU) 100, and a Processing Unit (PU) 200. FIG. 4 is an enlarged view of an inset in FIG. 3. The WU 100 ultrasonically (or inductively) powers the distributed network of the gastric seeds 300 regardless of their locations and orientations, and establishes bidirectional communication links with the gastric seeds 300 using two ultrasonic (US) transducers (power and data US in FIG. 5) or small coils. In some embodiments, each of the gastric seed 300 may communicate using an array of transducers. Each addressable gastric seed 300, when interrogated, records the differential-gastric SWs or/and injects predefined patterns of current into the tissue for stimulation from two capacitively or electrically coupled electrodes. The recorded signals are ultrasonically sent back to the WU 100, relaying data to the PU 200 for real-time mapping. Furthermore, an external beamforming platform in the PU 200 can ultrasonically reconstruct high-resolution images of GI motility in the user 10 by using the received ultrasonic pulses by each gastric seed 300.

Figure 5:
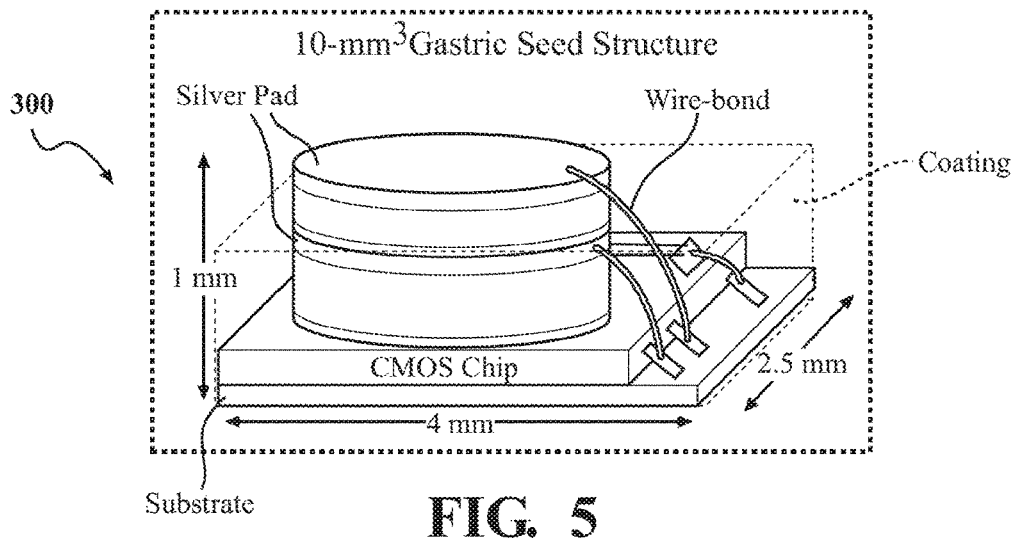
FIG. 5 is an enlarged view of a gastric seed according to an embodiment of this disclosure.

A distributed array of the gastric seeds 300 with an individual size of 4×2.5×1=10 $mm^3$ may be implanted inside the stomach's 310 submucosa space to record the gastric SWs or to stimulate stomach tissues. As shown in FIG. 5, each gastric seed 300 integrates a thinned Complementary Metal-Oxide-Semiconductor (CMOS) Application-Specific Integrated Circuit (ASIC) (example size: 3×2×0.15 $mm^3$) with a unique ID and either one shared (time multiplexed) power/data transducer or two stacked US transducers (power and data US) on a substrate, on the back of which two recording pads 330 are printed (see FIG. 6). The power US transducer wirelessly receives power along with amplitude-modulated interrogation data from the WU 100. The data US transducer wirelessly transmits the recorded SW signals to the WU 100 using narrow pulses. The ASIC can be flip-chip bonded to a thin polyimide substrate with two submillimeter-scale pads (example size: 0.5×0.2 $mm^2$), separated by a few millimeters (example: ~3 mm), for the differential SW recording or gastric tissue stimulation.

The main component of the external WU 100 can be a flexible printed-circuit board (PCB) in the form of a belly-band worn by the user 10. As shown in FIGS. 3-4, the WU 100 is an ultrasonic wireless power/data platform having an array of optimized external US power and data transducers 400. In some embodiments, the whole stomach of the user 10 may be covered with the WU 100 from all directions. In other embodiments, the user 10 may wear the WU 100 on any part of the body such that the WU 100 is able to communicate and power the implanted gastric seeds 300. The WU 100, a) generates a semi-homogenous ultrasonic-pressure intensity with high efficiency at the distributed gastric seed 300 locations for delivering a minimum power to each gastric seed 300 regardless of its location and alignment in the stomach with an optimal excitation of the external power US array that may be distributed along the bellyband, b) modulates the gastric seed 300 IDs on a power carrier (e.g. data rate of hundreds of kbps) for continuously interrogating the gastric seeds 300 one at a time, and c) recovers data pulses using the external data US transducers 400. The data pulses contain the SW signals sent by the gastric seeds 300. These SW signals are used to determine underlying bioelectrical gastric activity of the user and to image the location of the gastric seeds 300 with a millimeter resolution via delay-and-sum beamforming. The WU 100 also transmits the recorded SWs to the PU 200 using commercially available low-power RF transceivers.

The PU 200 is generally located a few meters from the user 10 to wirelessly receive the recorded SWs from the WU 100 for a real-time display and mapping of the stomach activity. In some embodiments, at least part of the PU 200 may be located remotely and the data from the WU 100 is bi-directionally transmitted to the PU 200 by any suitable means of communication. In a non-limiting example, the data from the WU 100 is transmitted over the internet to a remotely located central processing unit that acts as the PU 200. Such a PU 200 may process data/information from a plurality of WUs 100 simultaneously. The PU 200 may detect the SW event(s), and perform cycle clustering, activation mapping, and the calculations of the SWs frequency, velocity, and amplitude. The PU 200 also sends the desired stimulation parameters to the gastric seeds 300 via the WU 100.

Figure 6:
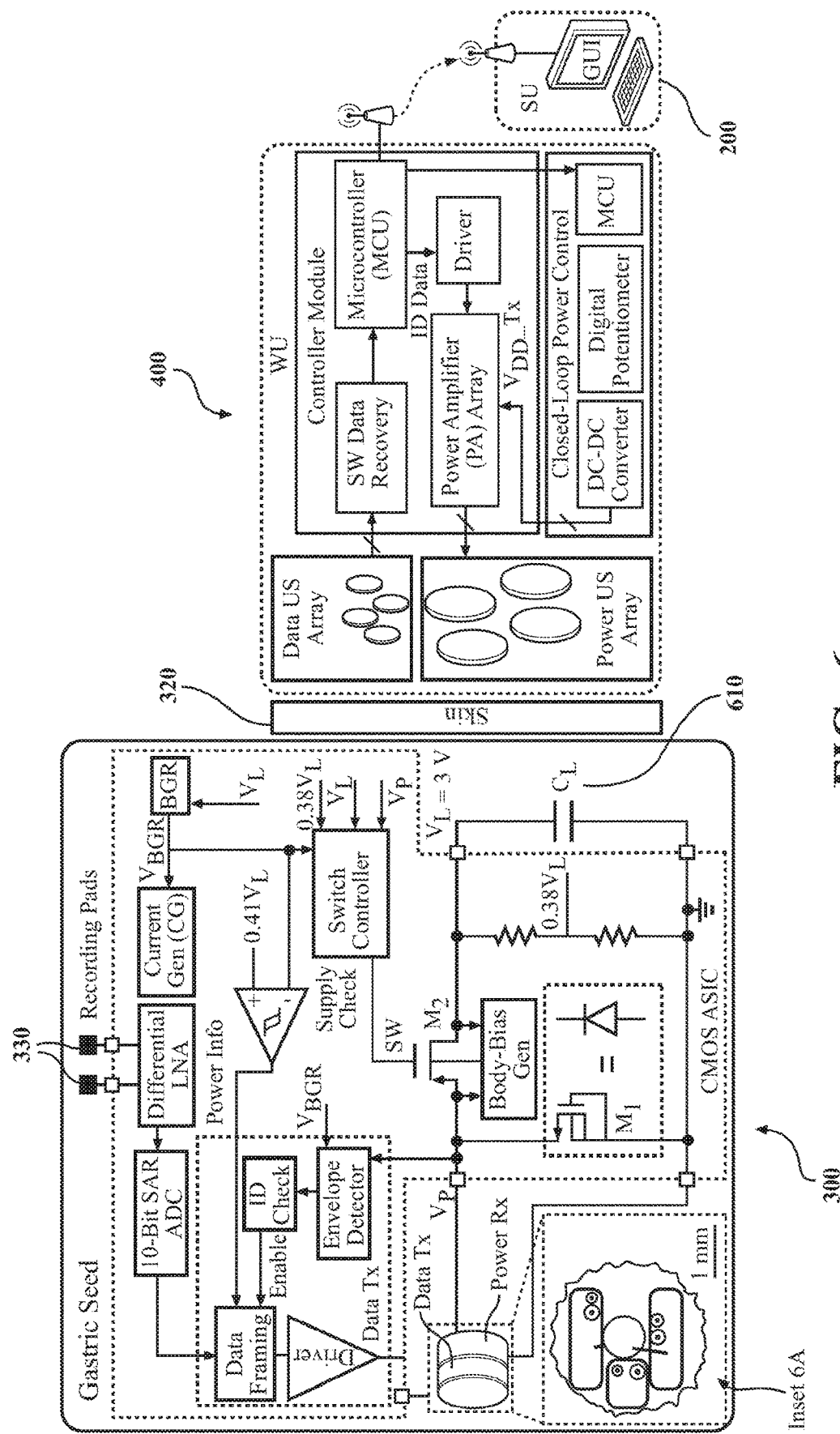
FIG. 6 is a block diagram of an embodiment according to this disclosure.

The working of an embodiment of the proposed technology is discussed below in reference to FIG. 6. FIG. 6 is a block diagram of the embodiment of the proposed technology that has a millimeter-scale gastric seed 300 implanted under the user's skin 320, a WU 400 and a PU 200. In the transducers 400 of the WU 100, a data recovery circuit receives the SWs from the gastric seeds 300 via an array of external US transducers 400. In the gastric seed 300 ASIC, a power management circuit provides power for the gastric seed 300, a clock/data recovery circuit demodulates incoming data (addresses and stimulation pattern), an analog front-end circuit amplifies/filters the SWs and digitizes them with an Analog to Digital Converter (ADC), and a stimulation circuit provides the stimulation current. Finally, a pulse-based (or carrier-based in general) data transmitter sends the SW data along with the gastric seed's 300 power information to the WU 100. The gastric seed 300 may be implanted in the user 10 by a suitable technique, including endoscopy.

A Wearable Unit (WU) 100 is generally worn over the user's skin 320 and is bi-directionally communicating with the gastric seed(s) 300. A Processing Unit (PU) 200 is placed either remotely or at a few meters away from the user 10 and is communicating bi-directionally with the WU 100. In the WU 100, the external power US transducers 400 are driven in a closed-loop fashion to provide sufficient and semi-homogenous ultrasonic power for all the gastric seeds 300 considering their worst-case powering distance and orientation. A multi-bit ID (10-bit for 1024 Seeds) of the first gastric seed (ID=0) is modulated on the power carrier and transmitted to all gastric seeds 300. The gastric seeds 300 receive power/data, check the ID, and if matched, that individual gastric seed 300 transmits its recorded signal along with the power supply information back to the WU 100. The rest of the gastric seeds 300 are also interrogated similarly in a predetermined order, until the last gastric seed is interrogated. This process is repeated to acquire the SWs from all the gastric seeds 300 in real time. Since the SWs are very low frequency (10-500 mHz), using a telemetry bandwidth of 100 kbps, at least 1000 gastric seeds 300 (i.e. 1000 recording/stimulation channels in the user's stomach) can be operated continuously if each gastric seed 300 is sampled at 5 Hz. The proposed technology can be scaled up by increasing the number of IDs and simultaneously interrogating the gastric seeds 300 located well apart. The received power information from each gastric seed 300 is used in the WU 100 to determine which gastric seeds 300 are receiving less power and to adaptively/locally increase or decrease the transmitted power.

FIG. 7 shows an experimental set-up used to demonstrate the technology of the present disclosure. The design, optimization, and implementation of ultrasonic links with Lead Zirconate Titanate (Pb[Zr(x)Ti(1-x)]O$_3$) (i.e. PZT) transducers for powering a single, stationary 1 mm$^3$ implant is shown in FIG. 7. In the proposed technology, an array of external power US transducers 400 of FIGS. 4 and 6 create a semi-homogenous ultrasonic pressure with high efficiency at the location of distributed gastric seeds 300. External and internal power transducers geometries (diameter, thickness, and matching materials), location/spacing of external power transducers 400, and the operation frequency may be optimized for a specific application/user. FIG. 8 shows preliminary simulations of ultrasonic beam intensity for two in-phase US transducers 400 operating in a far-field region which could provide intensities of >2 mW/cm$^2$ for a ~6×6=36 mm$^2$ area, compared to the small ~2×2=4 mm$^2$ area of a single US transducer (see FIG. 9). These simulations demonstrate a semi-homogenous ultrasonic intensity for a small area. The side beams of the adjacent transducers 400 can be used to improve power efficiency of the implanted gastric seeds 300 having some orientation, i.e. the implanted gastric seeds 300 are not fully aligned with the WU 100. These external US transducers 400, worn around the stomach, can provide ultrasonic power from all directions.

FIG. 6 shows a simplified diagram of the proposed gastric seed chip 300, including an analog front-end (AFE), a pulse-based data Tx, and self-regulated power management. The AFE may include a tuned low-noise amplifier (LNA) and a 10-bit successive approximation register analog-to-digital converter (SAR-ADC). The chip externally (or internally) requires one capacitor ($C_L$) 610 and a pair of stacked power/data ultrasonic transducers with 1.2 mm diameters, a proof-of-concept of which is assembled on a PCB as shown in FIG. 6A inset.

Self-Regulated Power Management

An integrated power management typically requires two large capacitors for rectification and regulation, and often an additional large capacitor for over-voltage-protection (OVP). In the case of a voltage doubler, even another large capacitor is also required. However, in a millimeter-sized gastric seed a minimum number of large capacitors should be used. As shown in FIG. 6, the proposed power management is in the form of a voltage doubler and can perform rectification, regulation and over-voltage-protection (OVP) in one step with only one off-chip (or on-chip) capacitor ($C_L$) 610. A switch controller block generates SW to control the pass transistor (M2) as an active switch. Considering the inherent internal capacitance of the power ultrasonic transducer (power Rx), the voltage doubler is formed by connecting the diode-connected transistor (M1) in parallel with the transducer. Therefore, this power management technically eliminates the need for 3 large capacitors.

Figure 13:
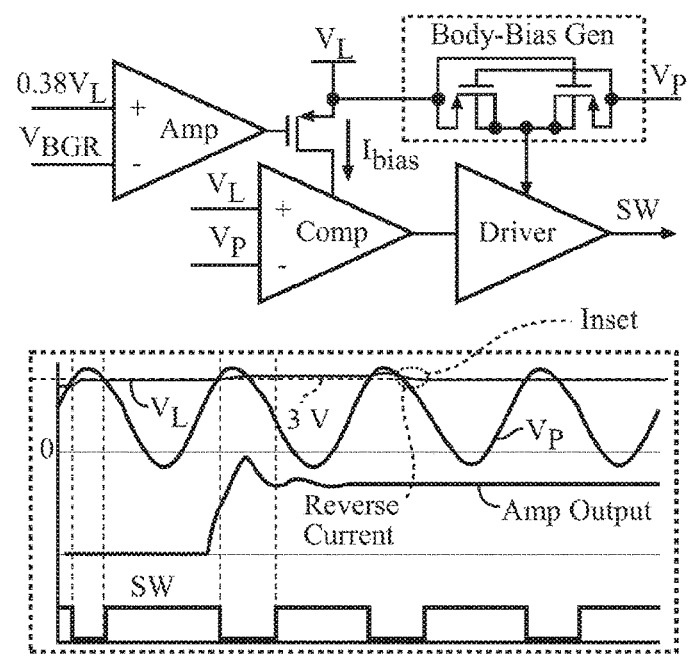
FIG. 13 is a schematic of a switch controller in power management and a graph showing operational waveforms of the switch controller.

FIG. 13 shows the switch controller schematic diagram along with its key operational waveforms for self-regulation of $V_L$ at 3 V utilizing reverse current from $C_L$ to the ultrasonic transducer. Inside the switch controller, an amplifier (Amp) controls the bias current ($I_{bias}$) of a comparator (Comp), comparing $V_L$ with the received voltage ($V_P$) as in an active rectifier, by amplifying the difference between $0.38 \times V_L$ and $V_{BGR}$=1.15 V. If $V_L$<3 V, the amplifier outputs low and IBIAS is maximized. Therefore, the comparator operates at its highest speed to maximize the forward current flowing from the ultrasonic transducer ($V_L$) to $C_L$ when $V_P > V_L$ and minimize the reverse current when $V_P < V_L$. This ensures the highest power conversion efficiency (PCE) in charging $C_L$. When $V_L$ surpasses 3 V, the amplifier reduces $I_{BIAS}$ that slows down the comparator during turn-off (increasing SW pulse width) and allows reverse current to flow from $C_L$ to the transducer (also loading the transducer), reducing $V_L$ as shown in FIG. 13 inset. This iterative process self-regulates $V_L$ at 3 V.

Addressable Pulse-Based Data Communication

To demonstrate the concept of addressable gastric seeds, the chip in FIG. 6 was designed to externally be assigned two IDs, "0" and "1". To enable IDs "0" and "1", the power carrier is modulated with a 20 µs activation notch followed by nothing or a second 20 µs notch after 5 µs, respectively. Upon activation, the gastric seed transmits 15 bits in the form of sharp pulses with 140 ns width for high bits and nothing for low bits (on-off keying modulation). These 15 bits include one bit for supply check (high: $V_L > 2.8$ V), 3 start bits ("101"), 10 digitized recorded data bits and one end bit (high).

FIG. 14 shows the schematic diagram and key operational waveforms of the address (ID) check block, in which the $V_P$ envelope is first recovered. Then, the rising edge of the activation notch (X), triggering FF1 flip-flip, is delayed by 15 µs (Y) to trigger FF2, detecting the address (addr) command of either "1" or "0". When addr is high, the gastric seed with ID="0" is enabled by setting S0_EN low and consequently Tx_EN$_0$ high as shown in the FIG. 14 waveforms. Similarly, the gastric seed with ID="1" is enabled when addr is low (Tx_EN$_1$: high). The START and RST signals in FIG. 14 are generated internally at the beginning and end of each 15-bit data frame.

Measurement Results

FIG. 15 shows the die micrograph of the proof-of-concept gastric seed chip, fabricated in a 0.35-µm 2P4M CMOS process, occupying 0.6 mm$^2$ and 0.4 mm$^2$ with and without pads, respectively. The chip operates at the power carrier frequency ($f_p$) of 1 MHz to regulate $V_L$ at 3 V ($C_L$=10 µF).

Figure 16A:
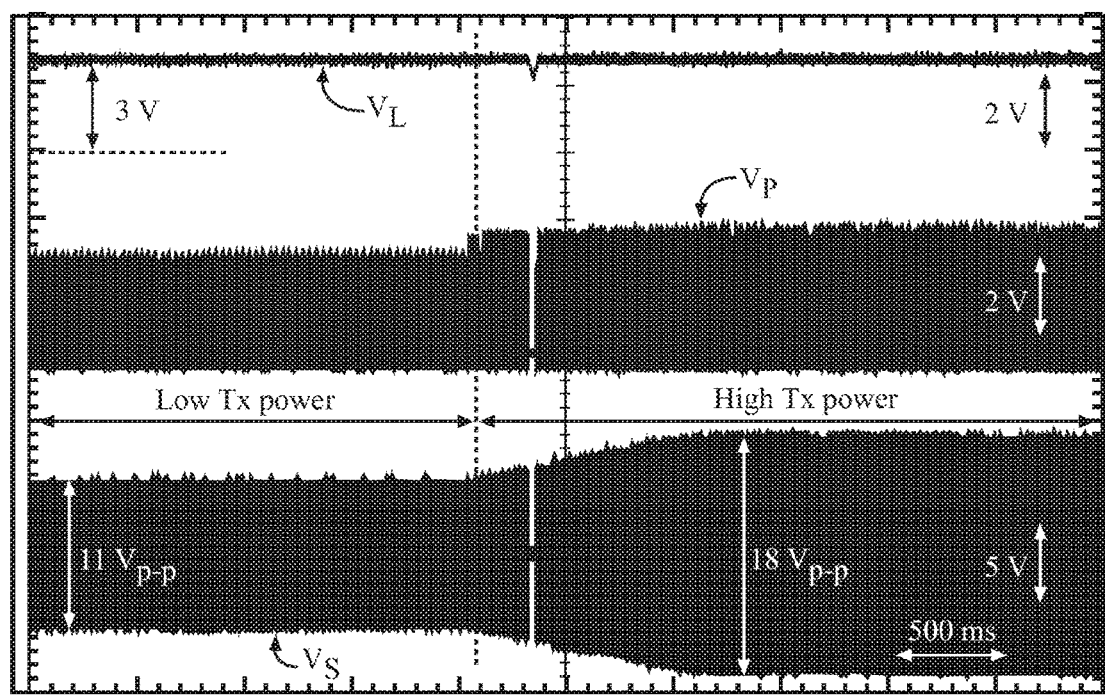
FIG. 16A is a graph showing measured waveforms of a power transducer and power management.
Figure 16B:
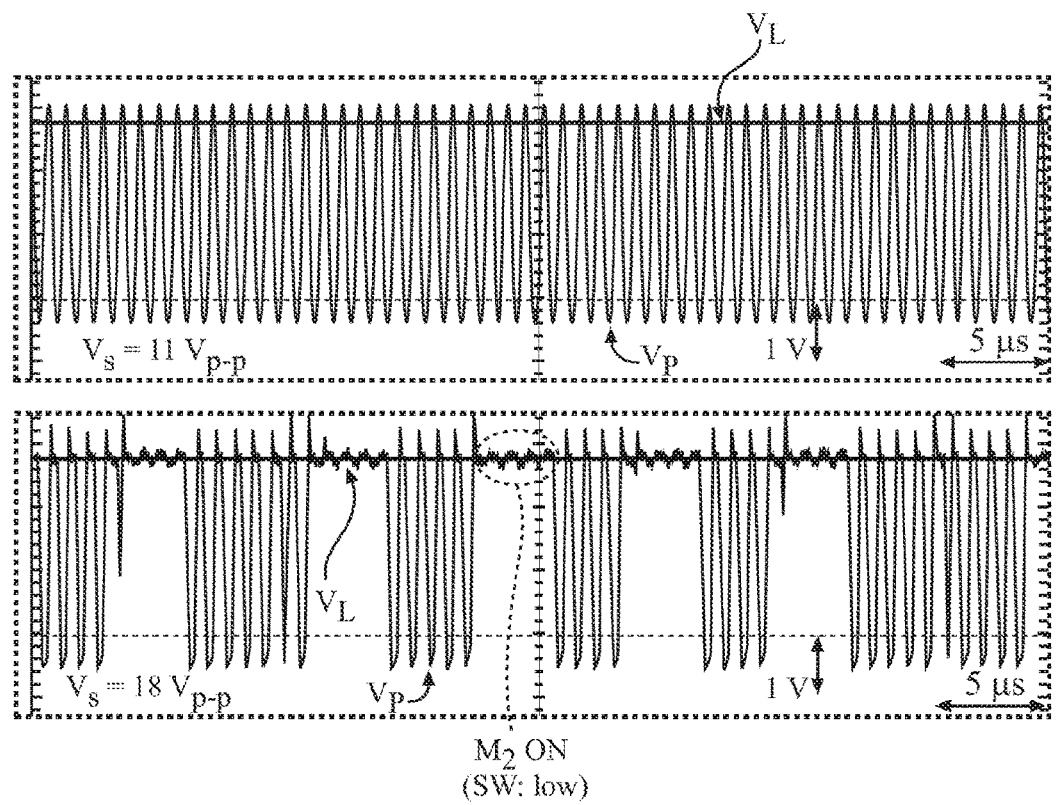
FIG. 16B is a graph showing a zoomed image of a part of the waveforms in FIG. 16A.

FIG. 16A shows the measured waveforms for the self-regulated power management in response to a sudden increase in the transmitted power (proportional to power Tx voltage, $V_S$). In FIG. 16A, when $V_S$ was increased from 11 Vp-p (peak-to-peak) to 18 Vp-p, the chip adaptively adjusted the width of SW pulses to maintain $V_L$ constant at 3 V with more frequent reverse currents. As shown in the zoomed waveforms in FIG. 16B, since the power Rx transducer has a large impedance of 5 kΩ at 1 MHz, limiting reverse current, at high $V_S$ of 18 Vp-p the chip even kept M$_2$ on (SW: low) for several power-carrier cycles to load the transducer with $C_L$ and limit the received power, regulating $V_L$ at 3 V. FIGS. 16A-16B also show voltage doubler proper operation by providing a DC shift across VP.

Figure 17:
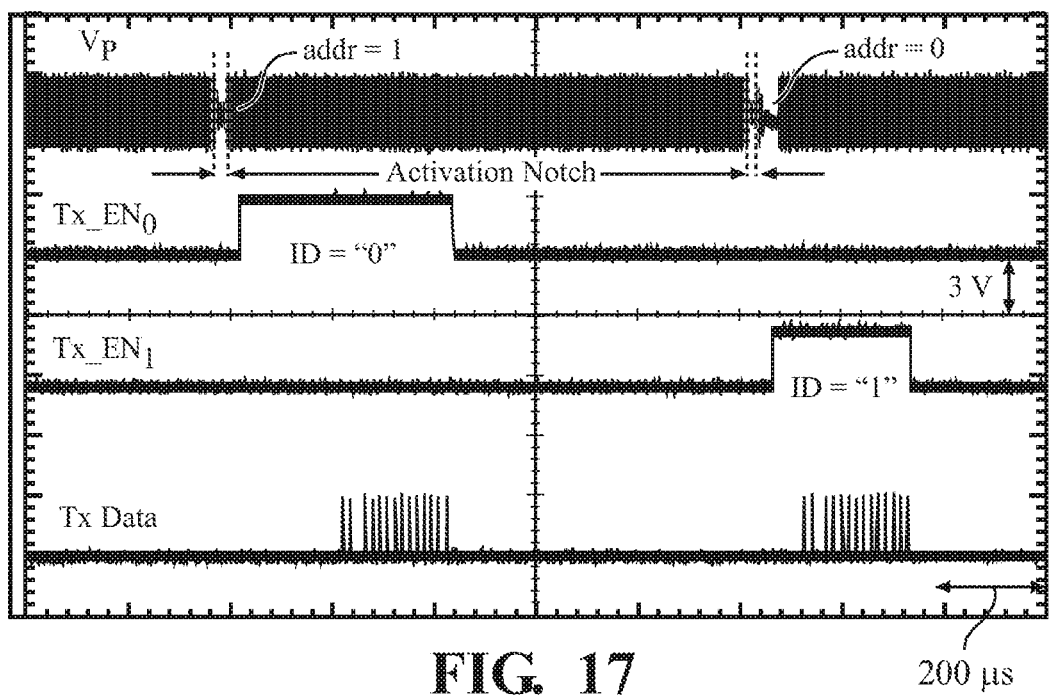
FIG. 17 is a graph showing measured waveforms of a data transmitter.

FIG. 17 from top to bottom shows the measured modulated $V_P$, Tx_EN$_0$, Tx_EN$_1$ and transmitted data pulses (Tx Data). In this measurement, $V_P$ was modulated for both IDs "0" and "1". When addr=1 (only activation notch) was detected, the gastric seed with ID "0" was enabled (Tx_EN$_0$: high) to transmit data pulses and vice versa.

Figure 18:
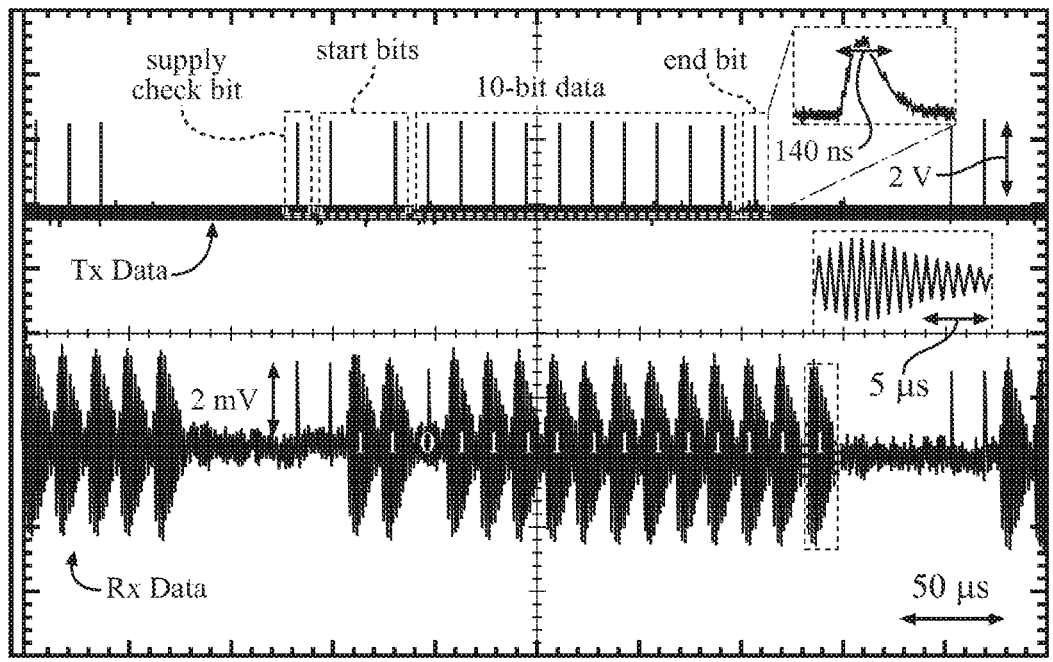
FIG. 18 is a graph showing a measured pulse-based data transmission of an ultrasonic transducer.

FIG. 18 shows measured pulse-based data transmission (15 bits) at the rate of 75 kbps using a pair of ultrasonic transducer spaced by 5 cm inside water, mimicking tissue. The width of each transmitted pulse was ~140 ns, which resulted in 440 pJ/bit energy consumption. Each pulse generated a ~15 µs voltage ringing at 1 MHz across the Rx data transducer.

Biocompatible barium titanate (BaTiO$_3$) piezoelectric material may be used in manufacturing the implantable gastric seeds 300. The diameter and thickness of the internal disk-shaped power transducers 400 are limited to millimeter scale. In earlier studies, 0.7% efficiency was achieved using a 1-mm diameter transducer working at 1.6 MHz located at a distance of 50 mm from the external US transducers (see FIG. 7). According to a non-limiting estimate, a worst-case efficiency of 0.1% could be achieved for the gastric seeds 300 considering their worst-case misalignment/orientation conditions. In one configuration, a small BaTiO$_3$ data US transducer is stacked on the power US transducer for pulse-based data transmission from the gastric seed to the WU (FIGS. 4 and 10). It should be noted that other embodiments might have different structural or physical configurations for the US data transducer and power US transducer, i.e. non-stacked configuration. Since a small transducer operates as a point source, the transmitted pulses by each gastric seed 300 are received by all external data US transducers 400 with different amplitudes and delays, which are used for imaging gastric seeds 300 locations via delay-and-sum beamforming. FIG. 11 shows wireless pulse-based data transmission with ultrasound at a distance of 5 cm.

The ASIC in each gastric seed 300 includes a power management circuit to provide a constant supply-voltage/power using an on-chip capacitor, a clock/data recovery circuit to detect the unique ID of each gastric seed 300 that is modulated on the power carrier, a memory with the stored specific ID, an analog front-end integrating low-noise amplifier/filter with the gain/bandwidth of 60 dB/10-500 mHz, an ADC, a stimulator block to provide differential current with adjustable pattern, and finally a pulse-based data transmitter.

Figure 12:
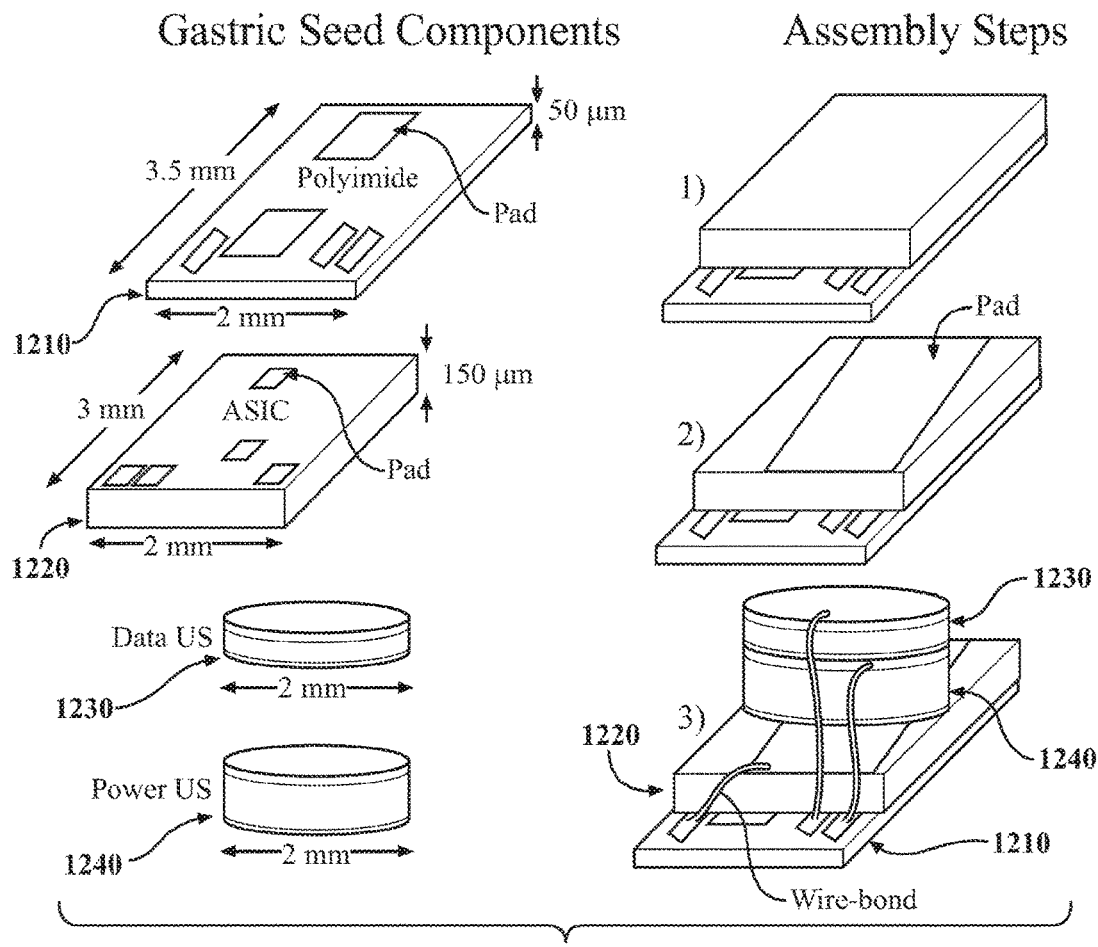
FIG. 12 shows an exploded view and assembly-steps for a gastric seed according to an embodiment of this disclosure.

FIG. 12 shows the exemplary steps for the assembly and packaging of the gastric seeds 300. A thin polyimide substrate 1210 (example size: 3.5×2×0.05 mm$^3$) with five gold pads for recording/stimulation, data, power, and ground are used as a platform to assemble the gastric seed 300. The ASIC 1220 with five (5) pads is flip-chip bonded to the polyimide substrate 1210 to make electrical contacts for the power (1240)/data (1230) US transducers and the recording/stimulation pads. A large copper pad is patterned on the backside of the ASIC for mounting the power US transducer 1240 with silver epoxy. This copper pad and the top silver plate of the power US transducer 1240 are electrically connected to the substrate with wire-bonds. Small amounts of silver epoxy are added to the top plate of the power US transducer 1240 for mounting the data US transducer 1230, which is also wire-bonded to the polyimide substrate 1210 (FIG. 10). Finally, the assembled gastric seed 300 is coated with the acoustically matched medical-grade UV-curable epoxy.

Although promising power transmission efficiency (PTE) results have been presented with fully aligned Tx and Rx transducers, an ultrasonic link is highly sensitive to the implant's misalignment, orientation, and even surrounding tissue medium. For instance, the ultrasonic link PTE in reduced from 10.6% to 0.12% (by 88 times) at d=10 mm for only 3 mm misalignment of the 1.1 mm$^3$ Rx transducer, which is quite inevitable in practical applications. This even gets more exacerbated as focused ultrasound via beamforming is used for wireless power transmission (WPT), in which the ultrasound intensity is focal, thus introducing more sensitivity to the implant's location. Therefore, focused ultrasound for WPT to mm-sized biomedical implants, particularly in the actively mobile peripheral nervous systems (PNS) organs, requires some kind of imaging to acquire prior knowledge about the implant's location.

The above-discussed imaging systems can be used to frequently image the implant's location and accordingly update the beamforming strategy. This imaging system is described below in reference to the above-discussed implanted gastric seeds. In some embodiments, the self-image-guided ultrasonic (SIG-US) technique (discussed below) is used as a practical ultrasonic WPT method. This technique results in lower power consumption, smaller size, reduced cost, and complexity. The proposed SIG-US technique can automatically adapt to the varying environment, such as the gastric seed's location and surrounding tissue medium, without having any prior knowledge, leading to robust, highly focused (efficient) beamforming for ultrasonic WPT.

In this disclosure, the SIG-US concept for powering a network of distributed gastric seeds in the body is discussed below. For proof of concept, finite-element method (FEM) simulation results are shown followed by conclusion remarks.

Self-Image-Guided Ultrasonic (SIG-US) WPT Concept

Figure 19:
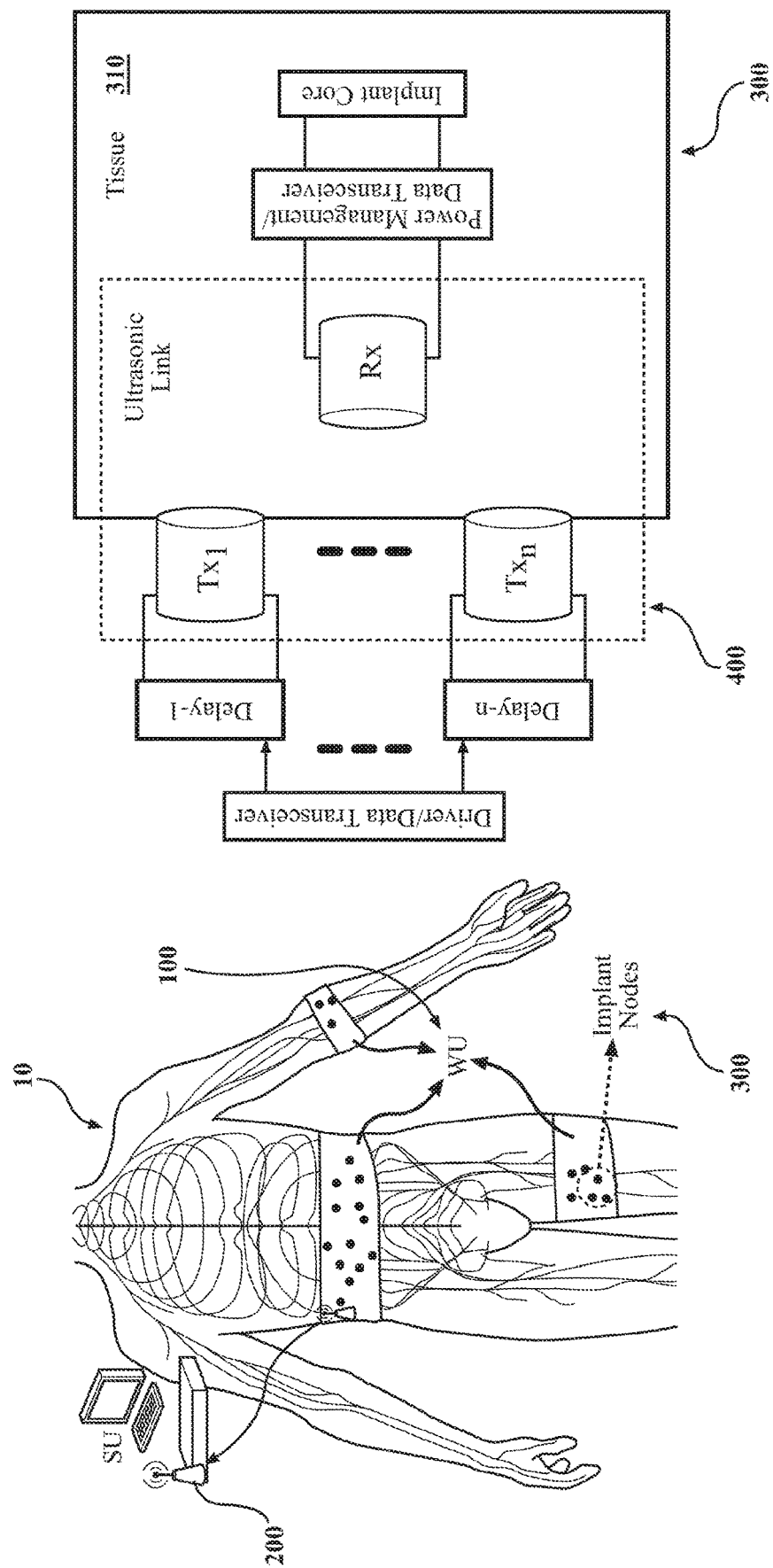
FIG. 19 is a schematic representation of a user with another embodiment of this disclosure (self-image-guided ultrasonic interrogation)

FIG. 19 shows the conceptual diagram of the proposed SIG-US WPT system for powering a network of mm-sized gastric seeds 300 as sensor or actuator nodes through optimal driving of external ultrasonic transducer arrays as a wearable unit (WU), which will communicate with a processing unit (PU) for data display and processing. Although, the SIG-US WPT system is discussed herein in reference to the gastric seeds, a person skilled in the art may use this system for other implantable medical devices that can interface with the central and peripheral nervous systems (CNS and PNS) to record and stimulate neuronal activity with different modalities, such as electric signals, light, and ultrasound. FIG. 19 shows the user with implanted mm-sized seeds 300 in the gastric region, antecubital/olecranal region and the femoral region. A person skilled in the art would be able to use this system for other implantable devices that are wirelessly powered and communicated. The WU, envisioned to be developed on a flexible (or rigid) printed-circuit board (PCB) in the form of bands worn by the user (to cover the targeted gastric seeds from all directions), will consist of an array of ultrasonic transducers 400 ($Tx_1$-$Tx_n$ in FIG. 19, n: number of transducers) driven by different delays as in a phased-array beamformer. Each gastric seed 300 is equipped with an ultrasonic transducer (Rx in FIG. 19) to recover power. The same Rx transducer or a separate transducer can be used for data communication.

The SIG-US WPT link works as follows: $Tx_1$-$Tx_n$ array is initially driven with pre-defined phases (based on approximate gastric seed's location) to provide some power for the gastric seed node at relatively low PTE. The power carrier is also modulated with the targeted gastric seed's ID. The gastric seeds, run at low-power mode by default, will receive power and data, check the ID, and if matched, the targeted gastric seed 300 transmits a sharp pulse back to the external array. This sharp pulse can be sent through the same Rx transducer or a separate data transducer. Since the mm-sized Rx transducer operates as a point source, the transmitted pulse will be received by all external transducers (either $Tx_1$-$Tx_n$ or a separate array of transducers for data) as a ringing with different amplitudes and delays, depending on the gastric seed's location, orientation, and surrounding tissue. These delays, which correspond to the image of the gastric seed 300, will be used for optimally driving the $Tx_1$-$Tx_n$ phased array to steer a highly efficient and focused beam towards the gastric seed regardless of its condition.

When the gastric seed receives power more efficiently, it will operate in the fully functional mode to record/stimulate neural activity. The sharp pulse for guiding WPT can be incorporated inside the transmitted data every 100's of milli-seconds (ms) or any shorter or longer time periods depending on the speed of environment movements. Therefore, the beamforming strategy can be updated every 100's of ms based on the gastric seed's condition in a closed-loop fashion, leading to robust operation. The proof-of-concept FEM simulation results for the SIG-US WPT to a single gastric seed are provided below.

Proof-of-Concept Simulation Results

Figure 20:
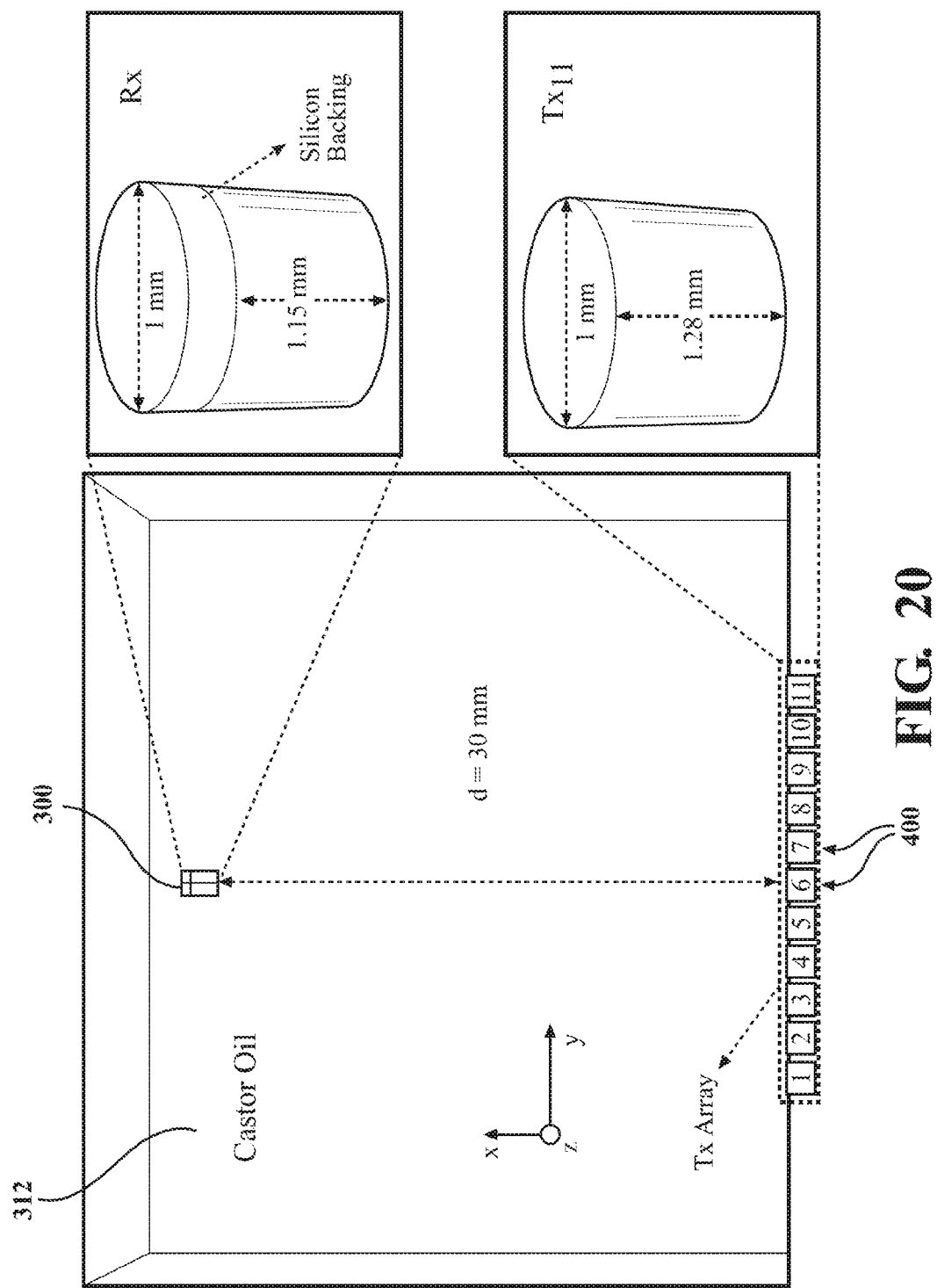
FIG. 20 is a schematic representation of a simulation set-up of another embodiment of this disclosure.

FIG. 20 shows a FEM simulation setup in COMSOL Multiphysics (COMSOL, Burlington, Mass.). A linear array of 11 ultrasonic transducers 400 ($Tx_1$-$Tx_{11}$) with the individual size of 1 $mm^3$ (diameter=1 mm) and center-to-center spacing of 1.5 mm were optimized to operate at 1 MHz for powering another optimized 1 $mm^3$ (diameter=1 mm) ultrasonic transducer 300 (Rx) located at d=30 mm inside castor oil 312. The Rx transducer 300 is backed with silicon to mimic the gastric seed's electronics. The castor oil 312 mimics the same acoustic impedance (1.4 MRayl) and loss (0.8 dB/cm/MHz) as the soft tissue.

Figures 21A, 21B:
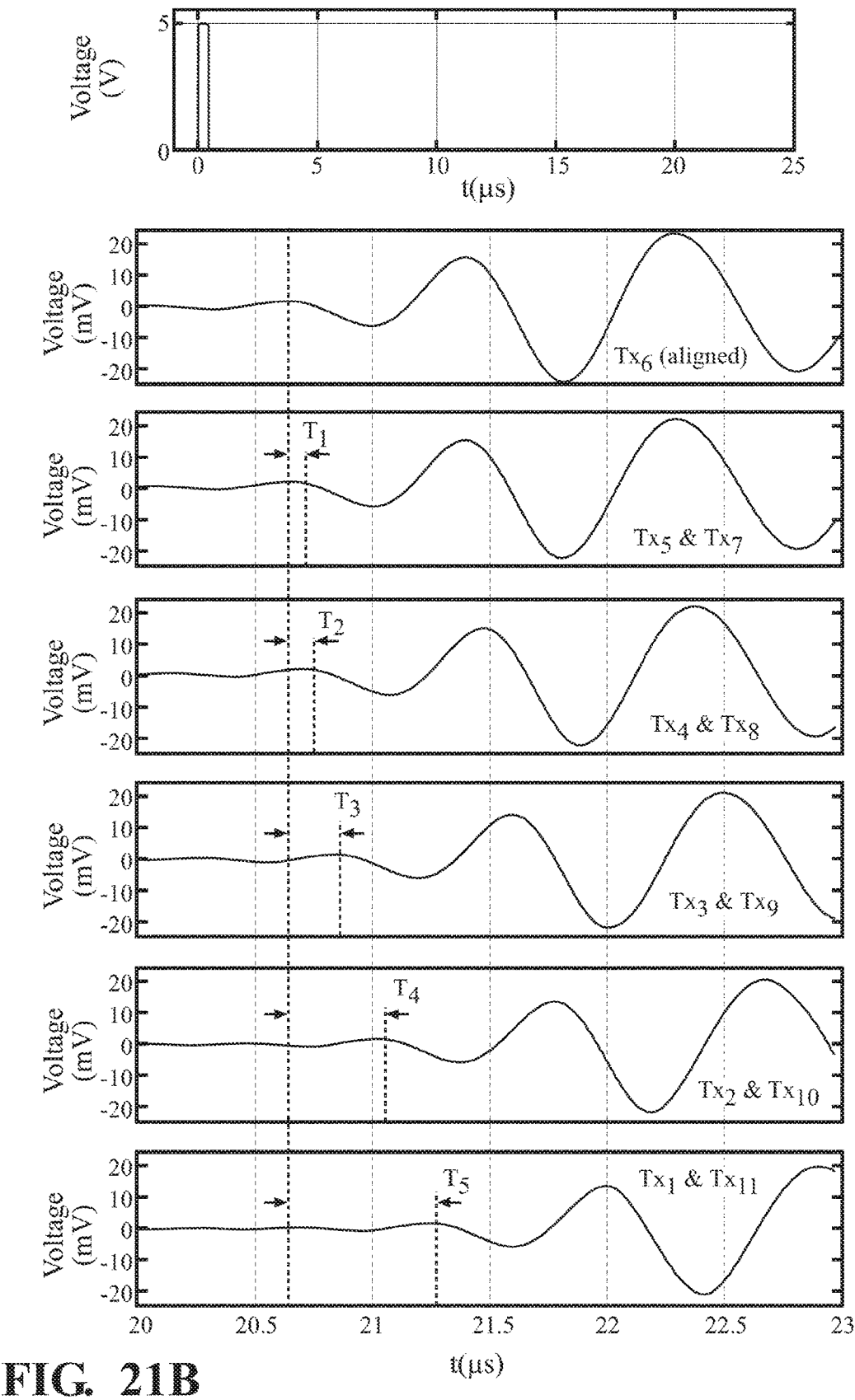
FIGS. 21A-21B are graphs showing a response of an external array to a pulse transmitted by an implanted transducer.

FIGS. 21A and 21B show the transmitted pulse by the implantable Rx transducer 300 with an optimal pulse width of 450 ns (for 1 MHz operation) and received ringings across external $Tx_1$-$Tx_1$ transducers 400 with different amplitudes and delays, respectively. FIG. 21B shows that the fully aligned $Tx_6$ transducer 400 with the least distance to the Rx transducer 300 received the transmitted pulse as a ringing with the smallest delay (~20.4 µs) and largest amplitude. From $Tx_6$ to $Tx_1$ (or $Tx_1$), the received ringing demonstrated more delay and lower amplitude due to the larger distance for ultrasound to travel.

Figure 22:
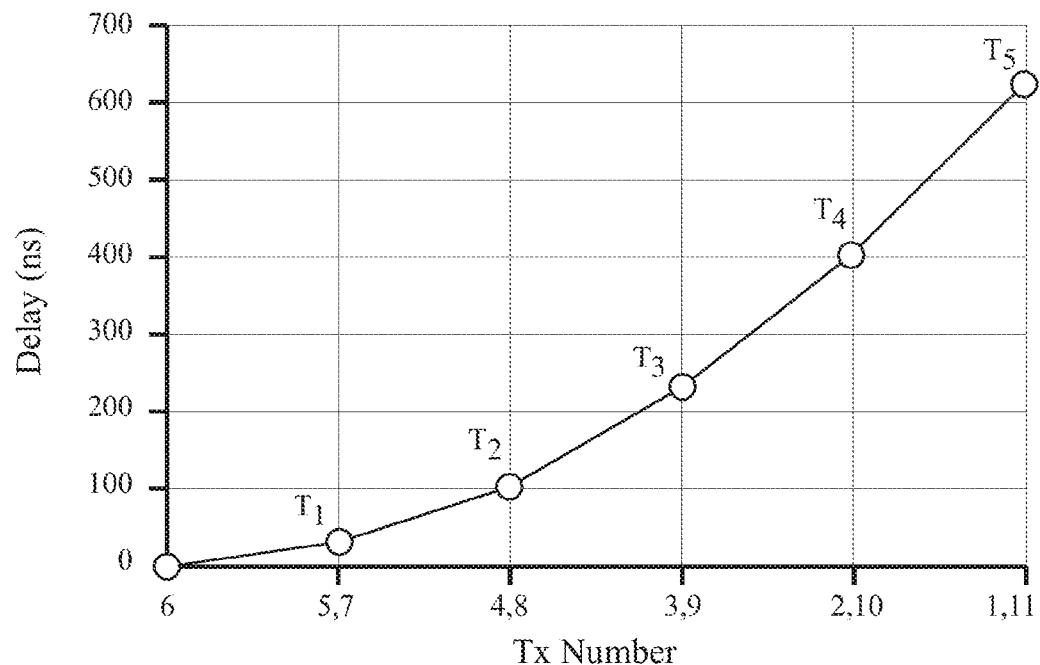
FIG. 22 is a graph showing relative delays of ringing received by each transducer of FIG. 20.

FIG. 22 shows the relative delays of the received ringings across Tx transducers 400 compared with fully aligned $Tx_6$, i.e., difference between $Tx_6$ delay with delays of $Tx_{1-5}$, $Tx_{7-11}$ in FIG. 21B. It can be seen that $Tx_1$ and $Tx_{11}$ have the largest delay of 620 ns while $Tx_5$ and $Tx_7$ have the smallest delay of 30 ns. These delays technically correspond to the image of gastric seed's location, which is used in the transmit beamformer.

Figure 23A:
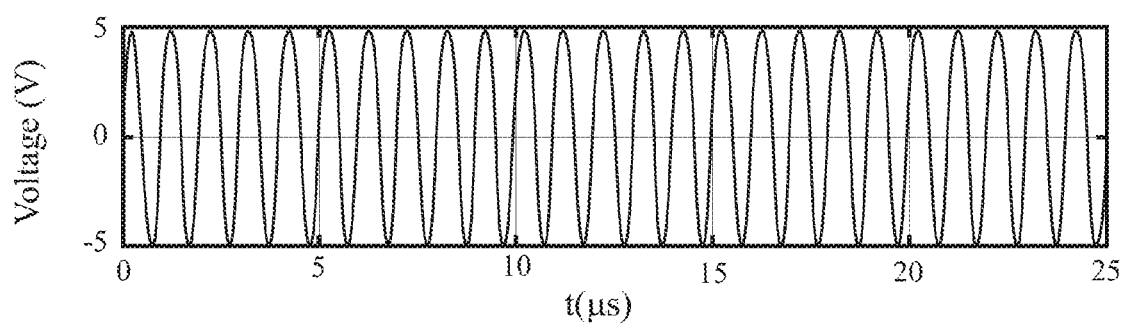
FIGS. 23A-23B are graphs showing a response of an external array to a sinusoidal carrier transmitted by the transducers of FIG. 20.
Figure 23B:
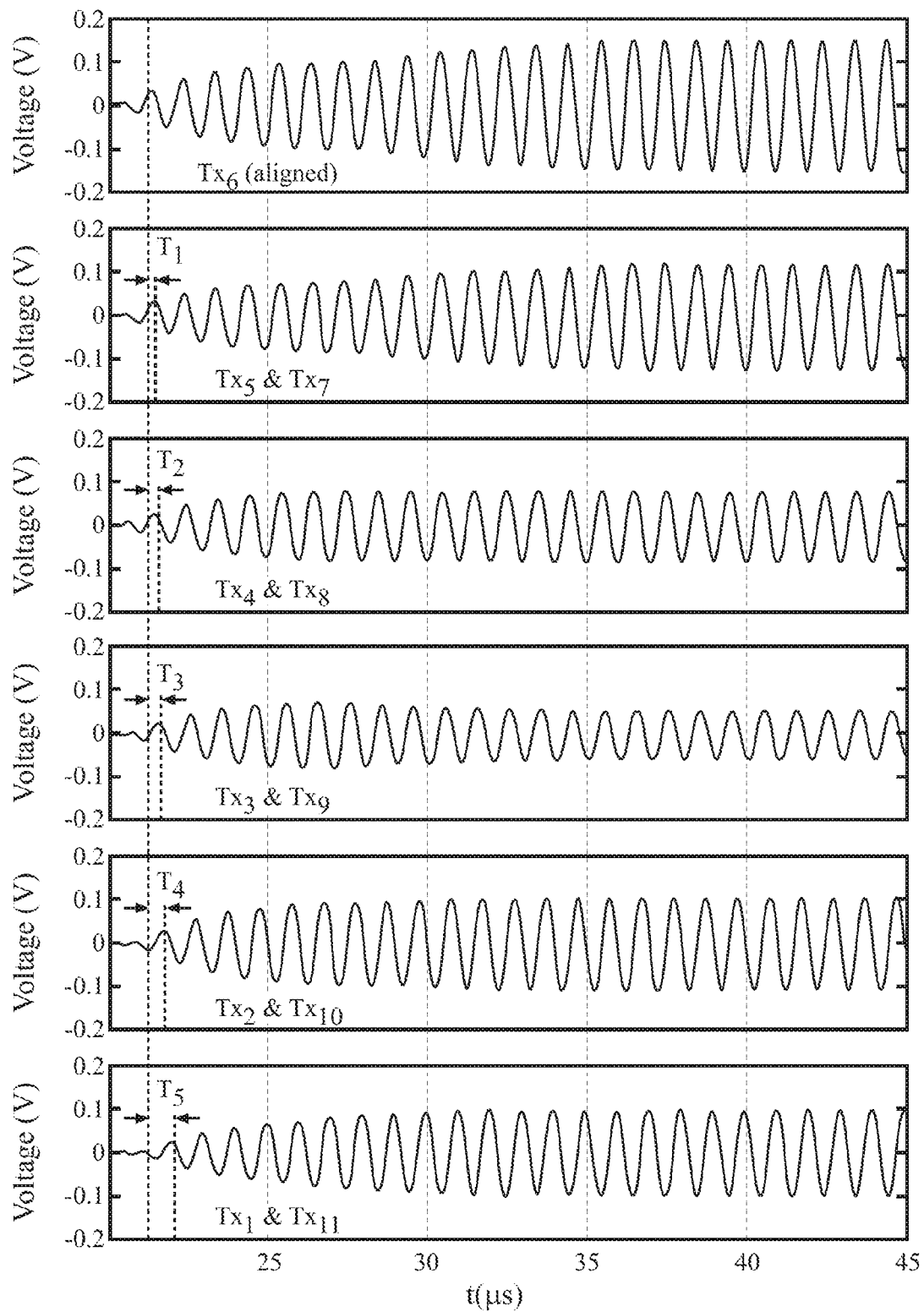

Based on the reciprocity theory, if the relative delays in FIG. 22 are inversely applied in driving the $Tx_1$-$Tx_{11}$ array with delayed sinusoidal carriers (i.e., driving $Tx_6$ with largest delay of 620 ns and $Tx_{1,11}$ with no delay), the received sinusoid by the Rx transducer due to each Tx transducer should add up in phase. In other words, beamforming is achieved without having prior knowledge of the gastric seed's location. However, first it should be examined that pulses and sinusoids lead to similar delays. FIG. 23A shows the 1 MHz sinusoidal carrier sent by the Rx that has resulted in sinusoidal signals with different delays and amplitudes across Tx transducers as shown in FIG. 23B. It can be clearly seen that the delays in FIGS. 21B and 23B match which is needed in SIG-US WPT.

Figure 24A:
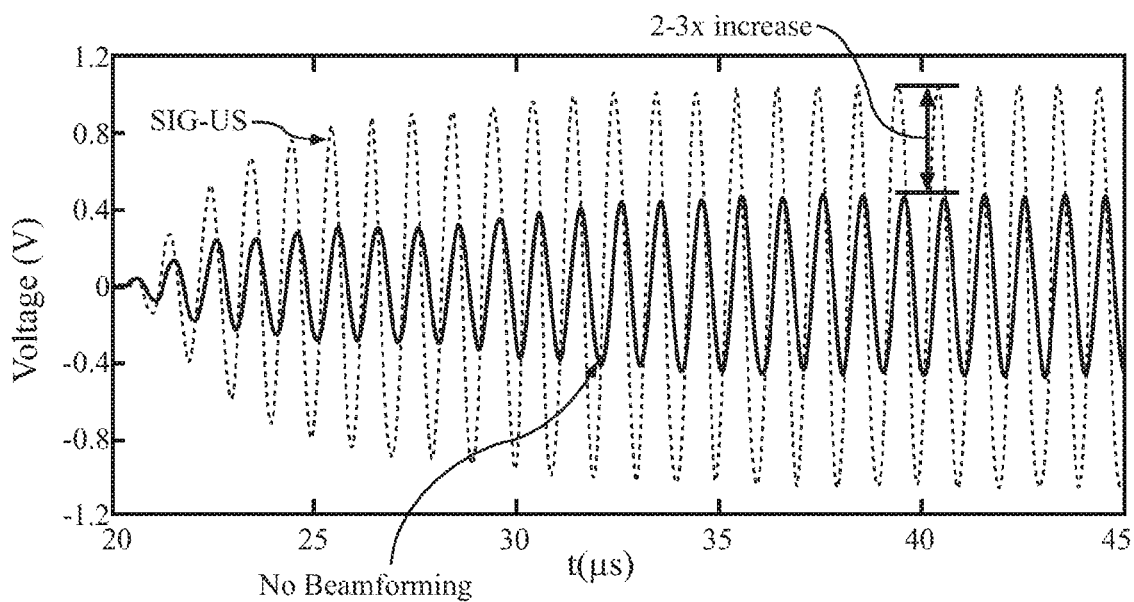
FIGS. 24A-24C are graphs showing the voltage received by a transducer.

FIG. 24A compares the received voltage by the Rx transducer at a fully aligned condition when $Tx_1$-$Tx_{11}$ transducer array was driven by sinusoidal carriers with SIG-US technique (beamforming using relative delays in FIG. 22) and without beamforming (in-phase excitation of $Tx_1$-$Tx_{11}$). As expected, the received voltage and consequently the delivered power by the SIG-US technique were 2.3 and 5.3 times higher, respectively, because the transmitted sinusoids were received and added in phase in the Rx.

To demonstrate the advantages of the proposed SIG-US technique over conventional beamforming, the Rx transducer was misaligned up to 6 mm (in Y-direction in FIG. 20). For SIG-US, at each misalignment, a pulse was transmitted from the Rx to the Tx array and relative delays in received ringings were found similar to FIG. 22. Then such optimal delays were inversely applied to the $Tx_1$-$Tx_{11}$ array. However, for conventional beamforming with no prior knowledge of the implant's location, fixed delays similar to fully aligned condition in FIG. 22 were used at different misalignments.

Figure 24B:
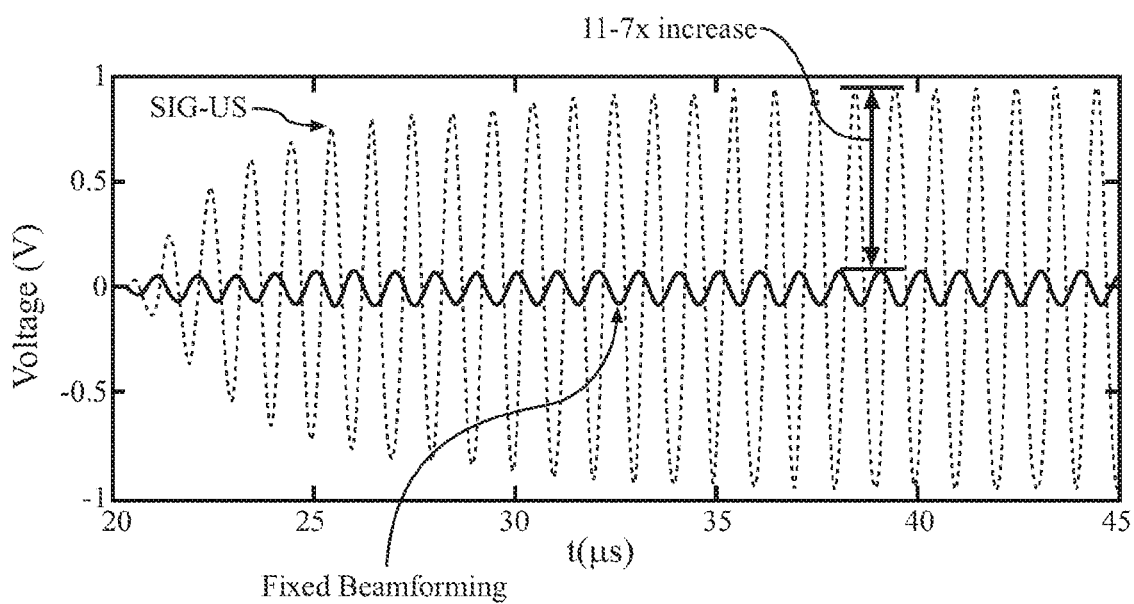
Figure 24C:
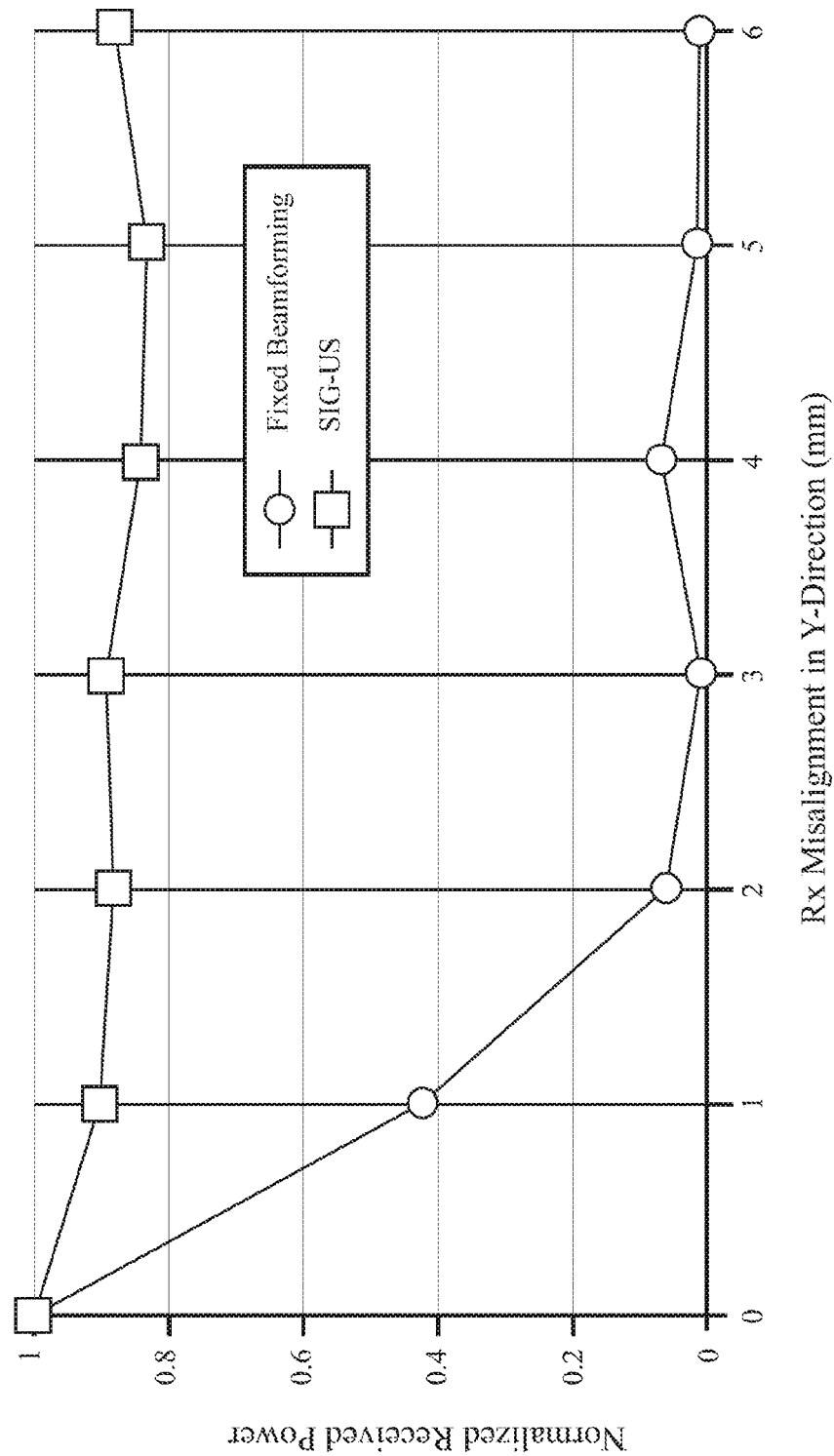

FIG. 24B compares the received voltage by the 3-mm misaligned Rx transducer with SIG-US and conventional beamforming. Since optimal beamforming delay values at 3 mm misalignment were achieved in SIG-US by transmitting sharp pulses, the received voltage and power were 11.7 and 136.9 times higher, respectively. FIG. 24C shows that for up to 6 mm Rx misalignment, the received power with the SIG-US technique only varied by 1.2 times compared with 156.3 times variation in the received power in conventional beamforming.

CONCLUSION

The proposed distributed millimeter-sized gastric seeds hold the promise of large-scale gastric SW recording with minimal damage. This disclosure has presented the concept of ultrasonically interrogated gastric seeds along with a proof-of-concept power management/data Tx chip. The prototype chip includes a self-regulated power management that performs rectification, regulation and OVP in one step using only one off-chip capacitor as well as an addressable pulse-based data Tx with a measured data rate of 75 kbps and energy consumption of 440 pJ/bit using a pair of 1 MHz ultrasonic transducers spaced by 5 cm in water. Based on this disclosure, a number of gastric seeds may be used for fully wireless recording capability with a robust ultrasonic interrogation platform.

The proposed SIG-US WPT technique provides robust and efficient ultrasonic WPT to networks of distributed, addressable mm-sized biomedical implants for interfacing with the body. The SIG-US technique can automatically and periodically locate the position and orientation of the implant in different tissue mediums to update the beamforming parameters in real time without the need for any sophisticated imaging system. This is especially useful if the location and orientation of the implanted device is constantly changing, i.e. an implant in a heart/stomach tissue. In proof-of-concept FEM simulations for 6 mm of implant's misalignment, 95.7 times improvement in received power was achieved by employing SIG-US compared with conventional beamforming with no knowledge of implant's movement. For up to 6 mm implant's misalignment, the received power variation with SIG-US was as low as 20%, which is quite significant.

Figure 25:
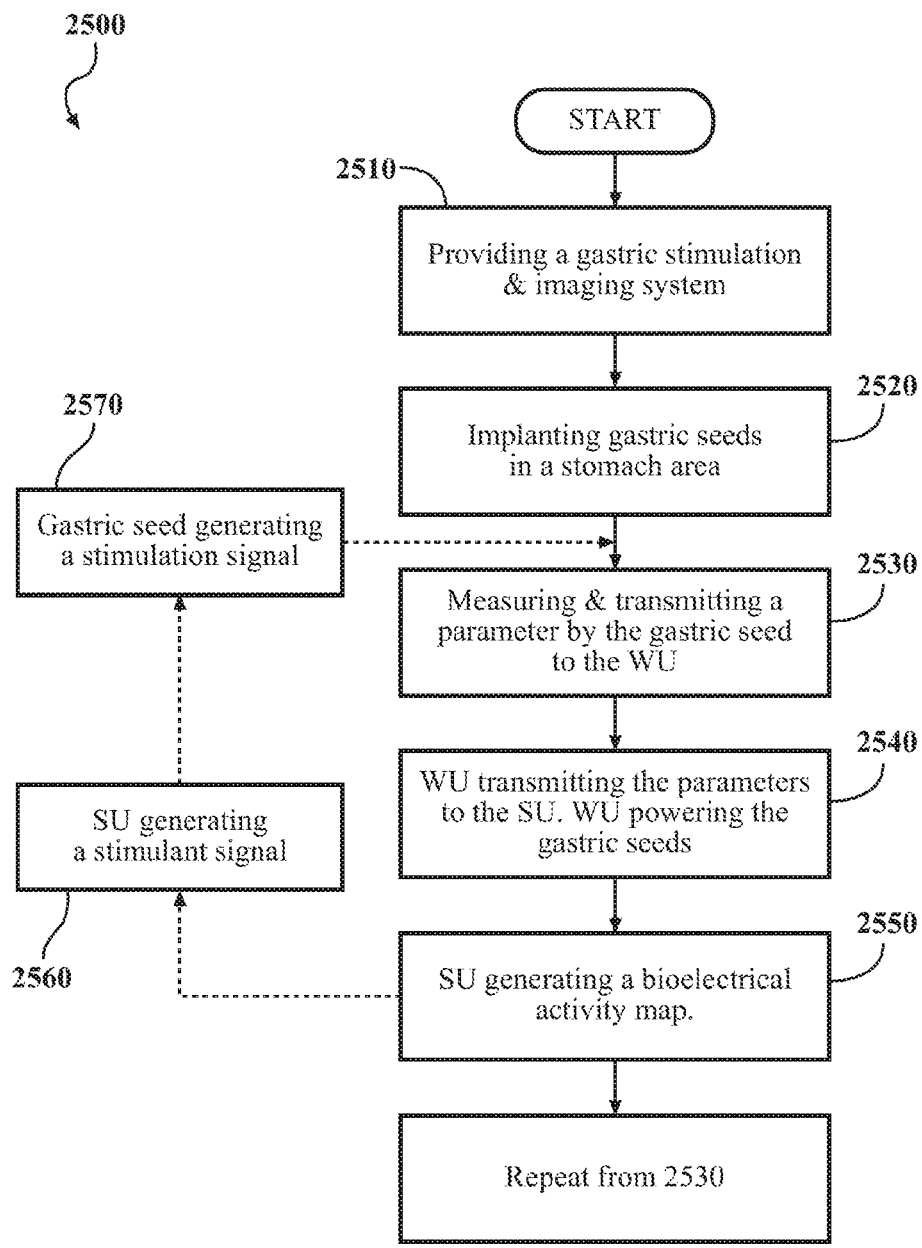
FIG. 25 is a flowchart showing a method of imaging and stimulating a gastric area of a user.

FIG. 25 is a flowchart showing a method 2500 of imaging and stimulating a gastric area of a user. The steps involved in the method 2500 are discussed below. These steps may be followed in another order than as shown in FIG. 25. A gastric stimulation and imaging system is provided at 2510. The above-discussed embodiments of the implantable gastric stimulation and imaging system of this disclosure may be provided at 2510. The array of millimeter-sized gastric seeds of the system is implanted in a stomach of a user at 2520. The gastric seeds are implanted in the submucosa or other layer of the stomach. In some embodiments, the gastric seeds are implanted in a plurality of layers of the stomach. Each gastric seed has a transducer with a recorder for recording a bioelectrical activity in the stomach.

The user either carries or wears a WU in the form of a bellyband. The gastric seeds measure parameters of a bioelectrical activity in the stomach area using the recorder of the transducer, and wirelessly transmitting the parameters from the gastric seeds to the WU using ultrasound at 2530. The WU wirelessly provides power to the gastric seeds using ultrasound, and wirelessly communicates the parameters from the WU to a processing unit (PU) using ultrasound at 2540. The PU generates a bioelectrical activity map of the stomach area based on the measured parameters at 2550. In some embodiments, these steps are repeated starting from the step of measuring & transmitting the parameter at 2530. In other embodiments, the PU generates a stimulant signal for the gastric seed based on the bioelectrical activity measured by that respective gastric seed at 2560. The PU wirelessly communicates the stimulant signal to the WU and the WU communicates the stimulant signal to the gastric seed. The gastric seed then generates a stimulation signal for the stomach based on the stimulant signal at 2570. In some embodiments, the WU provides power for the gastric seeds in a phased-array beamformer. According to the method 2500, the gastric seeds, WU and PU may communicate wirelessly and do not communicate using wires. The method may further provide pulse-based data transfer between the gastric seeds and the WU. In some embodiments, no other frequency except ultrasound is used for powering and communicating with the gastric seeds. The volume of each of the gastric seeds according to an embodiment of this disclosure may be in a range of 1 $mm^3$ to 10 $mm^3$. The PU may be remotely located with respect to the user.

The gastric seeds 300 may be made from other suitable materials, components, or may be assembled in a different configuration to achieve similar results as the above-discussed gastric seed 300. As will be clear to those of skill in the art, the herein described embodiments of the present invention may be altered in various ways without departing from the scope or teaching of the present invention. Accordingly, all such modifications are intended to be included within the scope of the embodiments of the present disclosure as defined in the following claims.

The invention claimed is:

1. An implantable acquisition/stimulation and imaging system for a user, comprising:
    an array of millimeter-sized seeds configured to be implanted in an area inside a user, each of the millimeter-sized seeds is ultrasonically powered and communicates using a transducer, the transducer having a recorder operable to measure a bioelectrical activity in the implanted area of the user;
    a wearable unit (WU) configured to be worn or carried by the user, the WU operable to wirelessly power the seeds, the WU operable to wirelessly communicate with the seeds, the seeds operable to communicate a parameter to the WU based on the bioelectrical activity; and
    a processing unit (PU) communicating with the WU, the WU operable to communicate the parameters from the seeds to the PU;

wherein each of the millimeter-sized seeds is identifiable by a unique address.

2. The system of claim 1, wherein the transducer further having a stimulator operable to generate a stimulation signal for the implanted area of the user, the PU communicating a stimulant signal to the seed via the WU, the PU operable to generate the stimulant signal based on the respective bioelectrical activity measured by that seed and communicated as the parameter to the WU.

3. The system of claim 2, wherein the stimulator comprises a capacitive and/or electrical electrode coupled to the implanted area tissues.

4. The system of claim 1, wherein the recorder comprises a capacitive and/or electrical electrode coupled to the implanted area tissues.

5. The system according to claim 1, wherein the WU comprises a flexible printed-circuit board (PCB) in a form of a band worn around the user's implanted area.

6. The system according to claim 1, wherein the ultrasonic power and/or ultrasonic communication signals are time-multiplexed.

7. The system according to claim 1, wherein the array of millimeter-sized seeds is implanted in a submucosa layer of the stomach, femoral region, antecubital region, olecranal region, or combinations thereof.

8. The system according to claim 1, wherein the WU comprises an array of ultrasound power and data transducers, the power transducers wirelessly powering the seeds, and the data transducers providing two-way communication between the seeds and the WU.

9. The system of claim 8, wherein the power transducers are powering the seeds in a phased-array beamformer.

10. The system according to claim 1, wherein the seeds, WU and PU communicate wirelessly and do not communicate using wires.

11. The system according to claim 1, wherein each of the seeds has a volume in a range of 1 $mm^3$ to 10 $mm^3$.

12. A method of imaging and stimulating a gastric area of a user, comprising the steps of:
providing a gastric stimulation and imaging system as claimed in claim 1;
implanting the array of millimeter-sized gastric seeds in a stomach area of a user;
the user wearing or carrying a wearable unit (WU);
measuring parameters of a bioelectrical activity in the stomach area using the recorder of the transducer, and wirelessly transmitting the parameters from the gastric seeds to the WU using ultrasound;
the WU wirelessly providing power to the gastric seeds using ultrasound;
wirelessly communicating the parameters from the WU to the processing unit (PU); and
the PU generating a bioelectrical activity map of the stomach area based on the measured parameters.

13. The method of claim 12, further comprising:
the PU generating a stimulant signal for the gastric seed based on the bioelectrical activity measured by that respective gastric seed;
the PU wirelessly communicating the stimulant signal to the WU;
the WU communicating the stimulant signal to the gastric seed; and
a stimulator of the gastric seed generating a stimulation signal for the stomach based on the stimulant signal.

14. The method according to claim 12, wherein the WU is providing power for the gastric seeds in a phased-array beamformer.

15. The method of claim 14, wherein the gastric seeds are implanted in a plurality of layers of the stomach of the user.

16. The method according to claim 12, wherein the gastric seeds, WU and PU are communicating wirelessly and do not communicate using wires.

17. The method according to claim 12, further providing pulse-based data transfer between the gastric seeds and the WU.

18. The method according to claim 12, wherein no other frequency except ultrasound is used for powering and communicating with the gastric seeds.

19. The method according to claim 12, wherein each of the gastric seeds has a volume in a range of 1 $mm^3$ to 10 $mm^3$.

20. The method according to claim 12, wherein the PU is remotely located with respect to the user.

21. An implantable acquisition/stimulation and imaging system for a user, comprising:
an array of millimeter-sized seeds configured to be implanted in an area inside a user, each of the millimeter-sized seeds is ultrasonically powered and communicates using a transducer, the transducer having a recorder operable to measure a bioelectrical activity in the implanted area of the user;
a wearable unit (WU) configured to be worn or carried by the user, the WU operable to wirelessly power the seeds, the WU operable to wirelessly communicate with the seeds, the seeds operable to communicate a parameter to the WU based on the bioelectrical activity; and
a processing unit (PU) communicating with the WU, the WU operable to communicate the parameters from the seeds to the PU;
wherein the ultrasonic power and/or ultrasonic communication signals are time-multiplexed.

22. The system according to claim 21, wherein the transducer further having a stimulator operable to generate a stimulation signal for the implanted area of the user, the PU communicating a stimulant signal to the seed via the WU, the PU operable to generate the stimulant signal based on the respective bioelectrical activity measured by that seed and communicated as the parameter to the WU.

23. The system according to claim 21, wherein the WU comprises a flexible printed-circuit board (PCB) in a form of a band worn around the user's implanted area.

24. An implantable acquisition/stimulation and imaging system for a user, comprising:
an array of millimeter-sized seeds configured to be implanted in an area inside a user, each of the millimeter-sized seeds is ultrasonically powered and communicates using a transducer, the transducer having a recorder operable to measure a bioelectrical activity in the implanted area of the user;
a wearable unit (WU) configured to be worn or carried by the user, the WU operable to wirelessly power the seeds, the WU operable to wirelessly communicate with the seeds, the seeds operable to communicate a parameter to the WU based on the bioelectrical activity; and
a processing unit (PU) communicating with the WU, the WU operable to communicate the parameters from the seeds to the PU;
wherein each of the seeds has a volume in a range of 1 $mm^3$ to 10 $mm^3$.

25. The system according to claim 24, wherein the ultrasonic power and/or ultrasonic communication signals are time-multiplexed.

26. The system according to claim 24, wherein the transducer further having a stimulator operable to generate a stimulation signal for the implanted area of the user, the PU communicating a stimulant signal to the seed via the WU, the PU operable to generate the stimulant signal based on the respective bioelectrical activity measured by that seed and communicated as the parameter to the WU.

* * * * *